US008830068B2

(12) United States Patent
Campbell et al.

(10) Patent No.: US 8,830,068 B2
(45) Date of Patent: Sep. 9, 2014

(54) MULTI-SENSOR ENVIRONMENTAL AND PHYSIOLOGICAL MONITOR SYSTEM AND METHODS OF USE

(75) Inventors: Vicki L. Campbell, Fort Collins, CO (US); Kevin L. Lear, Fort Collins, CO (US); Benjamin J. Vacha, Fort Collins, CO (US); Jarrod Zacher, Fort Collins, CO (US); Olivera K. Notaros, Fort Collins, CO (US)

(73) Assignee: Colorado State University Research Foundation, Fort Collins, CO (US)

( * ) Notice: Subject to any disclaimer, the term of this patent is extended or adjusted under 35 U.S.C. 154(b) by 196 days.

(21) Appl. No.: 13/233,887

(22) Filed: Sep. 15, 2011

(65) Prior Publication Data

US 2012/0068848 A1    Mar. 22, 2012

Related U.S. Application Data

(60) Provisional application No. 61/383,211, filed on Sep. 15, 2010, provisional application No. 61/391,903, filed on Oct. 11, 2010.

(51) Int. Cl.
| | | |
|---|---|---|
| *G08B 23/00* | (2006.01) | |
| *A61B 5/11* | (2006.01) | |
| *A61B 5/00* | (2006.01) | |
| *A61B 5/01* | (2006.01) | |
| *G08B 21/02* | (2006.01) | |

(52) U.S. Cl.
CPC .............. *A61B 5/01* (2013.01); *A61B 5/1118* (2013.01); *A61B 5/0008* (2013.01); *G08B 21/0211* (2013.01); *A61B 2560/0242* (2013.01); *G08B 21/0288* (2013.01); *A61B 2503/40* (2013.01); *A61B 5/7275* (2013.01)
USPC ..................................................... 340/573.1

(58) Field of Classification Search
CPC ....... A01K 29/005; A01K 29/00; A61B 5/02; A61B 1/00; A61B 5/00; A01J 3/00
USPC ........ 340/573.1, 539.27, 573.3, 815.4, 384.1; 600/549
See application file for complete search history.

(56) References Cited

U.S. PATENT DOCUMENTS

| | | | |
|---|---|---|---|
| 4,399,821 A * | 8/1983 | Bowers | 600/301 |
| 6,113,539 A * | 9/2000 | Ridenour | 600/300 |
| 6,198,394 B1 * | 3/2001 | Jacobsen et al. | 340/573.1 |
| 6,639,512 B1 | 10/2003 | Lee et al. | |
| 6,929,611 B2 | 8/2005 | Koch | |
| 7,081,811 B2 | 7/2006 | Johnston et al. | |
| 7,299,090 B2 | 11/2007 | Koch | |
| 7,348,880 B2 | 3/2008 | Hules et al. | |
| 7,705,736 B1 | 4/2010 | Kedziora | |
| 7,942,825 B2 | 5/2011 | Ranganathan et al. | |
| 8,085,144 B2 * | 12/2011 | Appelt et al. | 340/539.11 |
| 8,157,730 B2 * | 4/2012 | LeBoeuf et al. | 600/300 |
| 2002/0009119 A1 | 1/2002 | Matthew et al. | |
| 2007/0177651 A1 | 8/2007 | Daugherty et al. | |
| 2008/0058670 A1 * | 3/2008 | Mainini | 600/549 |
| 2008/0203178 A1 | 8/2008 | Barrett et al. | |

(Continued)

*Primary Examiner* — Phung Nguyen
(74) *Attorney, Agent, or Firm* — Polsinelli PC

(57) ABSTRACT

A system and method for monitoring the condition of a human, companion animal, or livestock animal in an extreme environment is disclosed. In particular, a system and method to process at least one environmental measurement and at least one physiological measurement to assess at least one condition of a human, companion animal, or livestock animal in an extreme environment is disclosed.

18 Claims, 15 Drawing Sheets

(56) References Cited

U.S. PATENT DOCUMENTS

| | | |
|---|---|---|
| 2009/0221884 A1 | 9/2009 | Ryan |
| 2009/0221888 A1* | 9/2009 | Wijesiriwardana ............ 600/324 |
| 2010/0036277 A1* | 2/2010 | Austin .......................... 600/549 |
| 2010/0282184 A1 | 11/2010 | Larson |

* cited by examiner

MULTI-SENSOR ENVIRONMENTAL AND PHYSIOLOGICAL MONITOR SYSTEM AND METHODS OF USE

CROSS REFERENCE TO RELATED APPLICATIONS

The present application incorporates in its entirety and claims the benefit under 35 U.S.C. §119(e) of: U.S. Provisional Application 61/383,211, filed Sep. 15, 2010 and titled "Canine Skin Temperature and Environmental Heat Index Sensor and Transmitter Collar"; and U.S. Provisional Application 61/391,903, filed Oct. 11, 2010 and titled "Canine Collar".

FIELD OF THE INVENTION

The present invention relates to devices and methods for monitoring the condition of a human, companion animal, or livestock animal in an extreme environment. More specifically, the present invention relates to devices and methods to process at least one environmental measurement and at least one physiological measurement to assess at least one condition of a human, companion animal, or livestock animal in an extreme environment.

BACKGROUND OF THE INVENTION

Hyperthermia or heat stroke is an ongoing threat to animals and children confined within enclosed vehicles and other extreme environments, especially during the warmer summer months. Soldiers, working military animals, companion animals and livestock may also be at risk of hyperthermia when living or working in extreme environments. For example, the temperature inside of the passenger section of a parked automobile may rise above 105° F. in less than 10 minutes and when the ambient outdoor temperature is greater than 88° F. Ambient temperatures routinely exceed 105° F. in some military deployment sites such as desert military stations.

To avoid hyperthermia in extreme environments, body temperature may be regulated by disposing of excess heat generated by exertion and/or basal metabolic activity. Conduction of internally generated heat to external body surfaces and evaporative cooling of surface fluids such as sweat are typically the primary means for animals to regulate body temperature. In some animals such as canines that do not generate sweat, respiratory evaporation may be the dominant mechanism of heat loss for body temperature regulation. The effectiveness of body temperature regulation in animals, in particular the efficiency of evaporative cooling, is sensitive to ambient environmental conditions.

High ambient temperatures and elevated humidity reduce the effectiveness of body temperature regulation. Regardless of temperature, when relative humidity exceeds 80% in an environment, the effectiveness of evaporative cooling is substantially reduced. High relative humidity in the ambient air around an animal may be a more critical factor than high temperature with respect to risk of hyperthermia, especially in animals such as canines that rely solely on respiratory evaporation for body temperature regulation.

Existing products monitor animals for signs of hyperthermia by measuring the ambient temperature inside of an enclosed environment such as the passenger compartment of an automobile. However, these existing devices generally only measure ambient temperature inside of the vehicle and fail to accurately measure or otherwise estimate the actual core or skin temperature of the animal. Further, these devices fail to account for variability in an animal's reaction to an extreme environment due to physiological factors, such as the animal's activity level, that may also vary depending on the particular species of animal.

A need exists in the art for a system for monitoring the condition of animals in extreme environments in which both environmental and physiological quantities are measured and processed to assess the animal's risk of developing a dangerous condition such as hyperthermia. A need in the art further exists for a monitor system, that include empirically-derived algorithms to estimate the condition of the animal based on environmental measurements, such as ambient temperature and relative humidity, and physiological measurements such as the animal's skin temperature and activity level. In addition, a need in the art exists for a monitor system that monitors a subset of a plurality of environmental and physiological sensor signals, in which the subset of signals includes non-redundant and/or high-quality signals. Such a system would be able to discern when an animal in an extreme environment is at risk of developing a dangerous condition such as hyperthermia or hypothermia and issue an alert to a caregiver or emergency response entity.

BRIEF SUMMARY OF THE INVENTION

A monitor system for monitoring at least one condition of an animal in an extreme environment is disclosed herein. The monitor system includes at least one physiological sensor to measure at least one physiological measurement from the animal and at least one environmental sensor to measure at least one environmental measurement from a region near the animal. The monitor system further includes at least one processor and a database that includes at least one threshold value. The at least one threshold value includes the maximum safe value of the at least one condition of the animal, and the at least one threshold value is a function of at least one condition of the animal.

The monitor system further includes an application executed by the processor to calculate the at least one condition of the animal by combining the at least one physiological measurement and the at least one environmental measurement. The application also retrieves the at least one threshold value and compare the at least one condition of the animal to the at least one threshold value and produces an alarm signal if the at least one condition of the animal exceeds the at least one threshold value.

In another embodiment, a method for monitoring at least one condition of an animal in an extreme environment is disclosed herein. The method includes receiving at least one physiological measurement from the animal and receiving at least one environmental measurement from a region near the animal. The method further includes retrieving at least one threshold value from a memory of at least one processor. The at least one threshold value comprises the maximum safe value of the at least one condition of the animal and the at least one threshold value is a function of at least one condition of the animal. The method further includes calculating at least one condition of the animal by combining the at least one physiological measurement and the at least one environmental measurement. The method also includes comparing the at least one condition of the animal to the at least one threshold value and producing an alarm signal if the at least one condition of the animal exceeds the at least one threshold value.

In an additional embodiment, a method for monitoring at least one condition of an animal in an extreme environment is provided. The method includes receiving a skin temperature and an accelerometer reading from the animal and receiving an ambient temperature and a relative humidity from a region near the animal. The method also includes retrieving a maximum core temperature. The maximum core temperature is a function of an animal activity level. In this method, the activity level of the animal is calculated by comparing the accelerometer reading to an animal activity rule, and a core temperature is calculated by substituting the skin temperature into a core temperature rule. The method also includes producing an alarm signal if the core temperature is greater than or equal to the maximum core temperature.

While multiple embodiments are disclosed, still other embodiments of the present invention will become apparent to those skilled in the art from the following detailed description, which shows and describes illustrative embodiments of the invention. As will be realized, the invention is capable of modifications in various aspects, all without departing from the spirit and scope of the present invention. Accordingly, the drawings and detailed description are to be regarded as illustrative in nature and not restrictive.

BRIEF DESCRIPTION OF THE DRAWINGS

Corresponding reference characters indicate corresponding elements among the views of the drawings. The headings used in the figures should not be interpreted to limit the scope of the claims.

DETAILED DESCRIPTION

Detailed descriptions of a monitor system, a collar monitor, methods of monitoring an animal's condition using a monitor system, and monitor system software are provided herein below. The monitor system may include one or more devices that each incorporate internal sensors and may receive additional information from one or more remote sensors. Wireless communication may be used to communicate sensor data between remote sensors and devices, as well as between individual devices. The sensors measure environmental data such as ambient temperature and relative humidity as well as physiological data such as skin temperature and movement.

1. Monitor System

Figure 1:
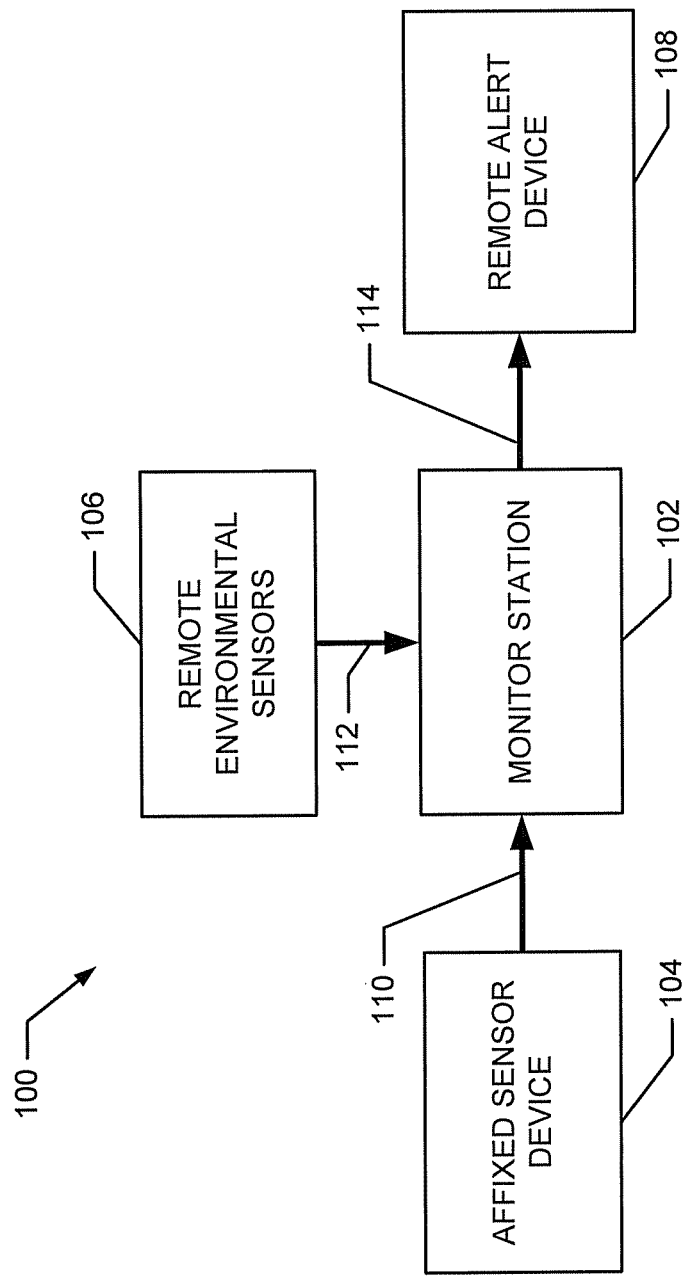
FIG. 1 is a block diagram illustrating the components of a monitor system.

Monitor systems for use in monitoring the condition and assessing the risk of harm to humans, companion animals, and livestock animals due to extreme environmental conditions and/or extreme exertion are disclosed herein. A block diagram of a monitor system 100 showing the relationship of the main system components is illustrated in FIG. 1. The monitor system 100 may include a combination of at least one or more components, and each component of the monitor system 100 may communicate with any one or more of the other components by means including but not limited to wireless and/or cellular signals to ensure accurate monitoring and user awareness of the animal's environmental and physiological condition.

As shown in FIG. 1, the monitor system 100 may include a monitor station 102. The monitor station 102 may be a self-contained and portable device that may process sensor data from internal environmental sensors housed within the monitor station 102 to assess the animal's environment and risk of developing adverse physiological conditions such as hyperthermia. In addition, the monitor station 102 may further incorporate sensor data received from an affixed sensor device 104 carried by the animal as well as sensor data received from one or more remote environmental sensor devices 106.

If the sensor data processed by the monitor station 102 indicates a potentially hazardous condition, the monitor station 102 may issue an alarm. The alarm may be a sensory alert such as an audible tone emitted by sensory alert devices contained within the monitor station. In addition, the alarm issued by the monitor station may generate a signal to command the production of an alarm by one or more other devices of the monitor system 100 including, but not limited to, the affixed sensor device 104 and a remote alert device 108.

The affixed sensor device 104 is a self-contained, portable device that may be affixed to the animal in order to monitor the skin or core temperature of the animal and the immediate environment near the animal. The affixed sensor device 104 may include one or more internal sensors to monitor environmental factors including, but not limited to, ambient temperature and relative humidity as well as physiological factors including, but not limited to, skin temperature and/or core temperature. The affixed sensor device may operate in a completely self-contained manner, or the affixed sensor device may operate in combination with the monitor station and/or remote environmental stations using wireless signals to communicate information between monitor system components. For example, the affixed sensor device 104 may independently process its internal sensor data and issue an alarm if the internal sensor data indicate a potentially hazardous condition. In another example, the affixed sensor device 104 may receive additional sensor data from the remote environmental sensor devices 106 and process the remote sensor data in combination with the affixed sensor device's 104 internal sensor data. In yet another example, the affixed sensor device 104 may transmit its internal sensor data to the monitor station 102 for analysis with no internal data processing.

One or more remote environmental sensor devices 106 may be incorporated into the monitor system 100 to provide additional information about the animal's environment. The one or more remote environmental sensor devices 106 may be any known environmental sensor, including but not limited to temperature sensors, relative humidity sensors, wind speed sensors, light sensors, carbon dioxide sensors, carbon monoxide sensors, ammonia sensors, smoke detectors, motion detectors, biohazard sensors, and any combination thereof. The one or more remote environmental sensor devices 106 include the capability to transmit the sensor data to other components of the monitor system 100, including but not limited to the monitor station 102 and the affixed sensor device 104.

The monitor system 100 may further include a remote alert device 108 that may be a portable signaling device such as a fob that is carried by a user of the monitor system 100. The remote alert device 108 may receive signals from the monitor station 102 and/or the affixed sensor device 104. In response to these received signals, the remote alert device 108 may issue a sensory alert such as an audible tone or visible light signal to the user carrying the remote alert device 108. The sensory alert issued by the remote alert device may indicate a variety of environmental and/or physiological conditions estimated by the monitor system 100 including but not limited to a tolerable condition, a potentially dangerous condition, or an emergency condition. For example, a potentially dangerous environmental condition may be a combination of temperature and humidity in which extended exposure may result in an increased risk of developing an adverse medical condition including but not limited to hypothermia, hyperthermia, frost bite, heat stroke, unconsciousness, adverse myocardial events, or death.

The monitor system 100 may be implemented in any one of at least several arrangements in addition to the arrangement illustrated in FIG. 1. For example, the monitor station 100 may be used without any additional system components to monitor an environment using its internal environmental sensors, and alerts may be issued directly from the monitor station 100. In another example, one or more remote environmental sensor devices 106 may be linked to the monitor station 106 to provide additional information about the environment. In yet another example, if the affixed sensor device 104 is in communication range of the monitor station 102, the affixed sensor device 104 may provide additional sensor data for the monitor station 102. In yet another example, if the user is away from the monitor station 102 and the animal is outfitted with an affixed sensor device 104, the remote alert device 108 may be carried with the user and used to monitor the environment and physiological condition of the animal. IN yet another example, if the affixed sensor device 104 is attached to a human subject, such as a soldier working in an extreme environment, the affixed sensor device 104 may be used without any additional system components.

The monitor system 100 may include software to determine the availability and quality of sensor data received from the various system components. This software may further determine any dangerous environmental and/or physiological conditions based on the available sensor data, along with information on sensor parameters corresponding to dangerous conditions.

The individual components of the monitor system 100 and the software included in the system's components are described in detail below.

a. Monitor Station

Figure 2:
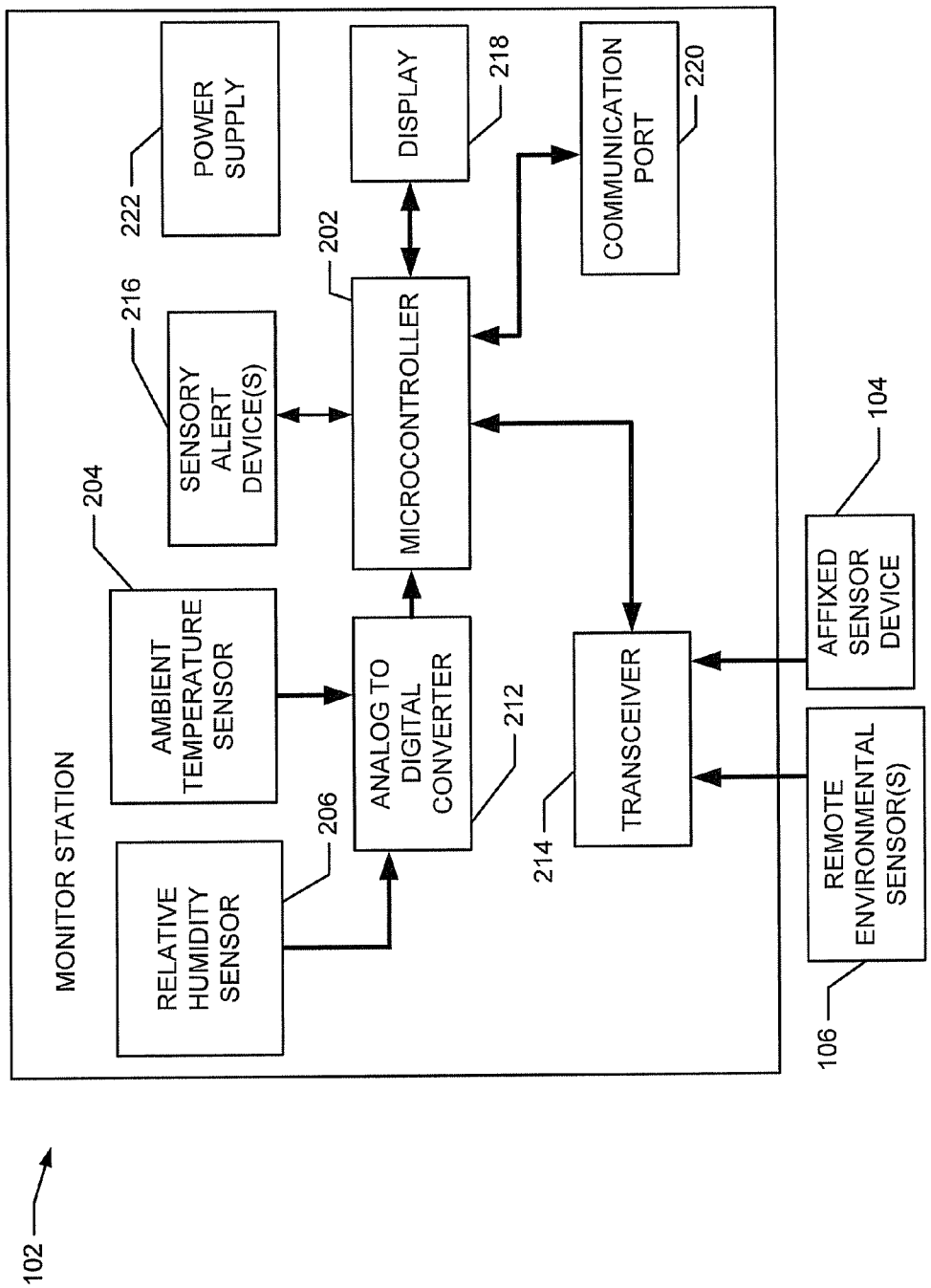
FIG. 2 is a block diagram showing the sub-components of a monitor station.

The monitor station 102 is a portable device that may serve as the central component of the monitor system 102 for receiving and processing sensor data and issuing alert signals based on assessment of the sensor data. FIG. 2 is a block diagram illustrating an arrangement of various sub-components of a monitor station 102. The monitor station 102 may include a microcontroller 202 that may contain stored instructions and one or more processors for implementing the various functions of the monitor station 102 described in detail below.

The microcontroller 102 may receive and process sensor data from a variety of internal and external sensor sources. The monitor station 102 may include one or more internal sensors including, but not limited to, an ambient temperature sensor 204 and a relative humidity sensor 206 to measure environmental variables that may indicate dangerous environmental conditions. The sensor signals from the ambient temperature sensor 204 and the relative humidity sensor 206 may be combined into a heat index, a perceived temperature or other known environmental measure using known methods.

The ambient temperature sensor 204 may be any known temperature sensor, including but not limited to a thermocouple, a digital temperature sensor, and a thermistor. The temperature sensor 204 included in the monitor station 102 may be selected on the basis of any one or more criteria, including but not limited to ruggedness in extreme environments, operational temperature range matched to the expected temperature range in use, relatively low power consumption, relative high accuracy and precision, compatibility of the sensor output with the microcontroller 202. The relative humidity sensor 206 may be any known sensor, including but not limited to chilled mirror dewpoint hygrometers, capacitive humidity sensors, resistive humidity sensors, and thermal conductivity humidity sensors. Alternatively, the ambient temperature sensor 204 and the relative humidity sensor 206 may be combined into a single sensor.

Depending on the particular type of internal sensors incorporated, an analog to digital converter 212 may be included to convert the output of the ambient temperature sensor 204 and the relative humidity sensor 206 into a format usable by the microcontroller 202. Alternatively, the microcontroller 202 may include internal analog to digital conversion capability. In addition to the internal sensors, the monitor station may further receive sensor data from other devices of the monitor system 100, including, but not limited to, the one or more remote environmental sensor devices 106, and the sensors of the affixed sensor device 104. The sensor data from these other devices of the monitor system 100 may be received by a transceiver 214 included in the monitor station 102. Depending on the nature of the signal received by the other devices (i.e. analog or digital signals), the signals received through the transceiver 214 may be processed by either the analog to digital converter 212 or by a microcontroller-based analog to digital conversion function resident in the microcontroller 202 prior to further processing by the microcontroller 202.

The microcontroller 202 may generate an alert if the processed sensor data indicate a dangerous environmental or physiological condition. This alert may be sent to a sensory alert device 216 included in the monitor station 102. In response to the alert signal from the microcontroller 202, the sensory alert device 216 may produce a sensory alert signal to indicate to the user that a dangerous environmental or physiological condition has been detected. Non-limiting examples of suitable sensory alert signals include audible tones, visible light signals, alphanumeric displays, vibrations, and combinations thereof.

The alert generated by the microcontroller 202 may be transmitted to other system components including but not limited to the affixed sensor device 104 and remote alert device 108. Upon receiving an alert generated by the microcontroller 202 of the monitor station 102, these other system components may produce similar sensory alert signals. Alternatively, the alert generated by the microcontroller 202 may be transmitted to third-party devices including but not limited to cellular telephone devices, pager devices, and remote computing devices via the transceiver 214. In this example, the signal transmitted to the third-party devices may be in any known form including, but not limited to, page messages, text messages, cellular phone calls, emails, and voicemails.

The monitor station 102 may further include a display 218 to provide the user with an indication of the current environmental and or physiological conditions as assessed by the algorithms of the monitor station 102. Non-limiting examples of suitable displays include alphanumeric displays such as LED or LCD displays, color-coded lights, variable-height bar displays, dials, and any other suitable visual display known in the art. For example, the display 218 may be an alphanumeric display that communicates the current estimated ambient temperature and relative humidity as assessed by the monitor station 102 to the user. As another example, the display 218 may emit light a colored light signal such as a green light to indicate tolerable environmental conditions, a yellow light to indicate a high likelihood of dangerous environmental conditions, and a red light to indicate that dangerous environmental conditions were indicated by the sensor data. The display 218 may be updated essentially continuously, or the display may be updated periodically at any selected time interval.

The monitor station 104 may also include a communication port 220 to provide a variety of interface functions including, but not limited to, programming or trouble-shooting the microprocessor 202, and uploading or downloading data and/or instructions to the microprocessor 202.

The monitor station 104 may also include a power supply 222. Although any known power supply may be used, the power supply may be selected to be a portable power supply in order to enhance the portability of the monitor station 104. Non-limiting examples of devices suitable for use as a power supply 222 include single-use batteries, rechargeable batteries, batteries integrated into vehicles, solar power units, miniature wind-driven units, or other supplies of electrical power that may be incorporated in or connected to the monitor station 104. In addition, when multiple power sources are available, the power supply 222 may actively manage the power sources by assessing the readiness (e.g., charge state, voltage, and/or available current) of available power sources and selecting among power sources that meet the electrical supply requirements of the power supply 222. The power supply 222 may further include the ability to replenish the stored charge energy storage devices including but not limited to batteries. For example, the power supply 222 may be connected to an external power source for operation and charging of internal batteries. The power supply 222 of the monitor station 102 may also recharge other devices in the monitor system 100, including but not limited to the remote environmental sensor devices 106, the affixed sensor device 104, and the remote alert device 108.

b. Affixed Sensor Device

The affixed sensor device 104 of the monitor system 100 may be attached to and/or carried by the animal, and may provide sensor measurements of environmental and physiological quantities in close proximity to the animal to the monitor system 100. Unlike the sensors resident in the other devices of the monitor system 100, which are typically stationary, the sensors within the affixed sensor device 104 travel with the animal. The affixed sensor device 104 may be attached to the animal by any known means of attachment including, but not limited to a band, collar, adhesive, sutures for the purpose of directly monitoring the animal in any environment.

Figure 3:
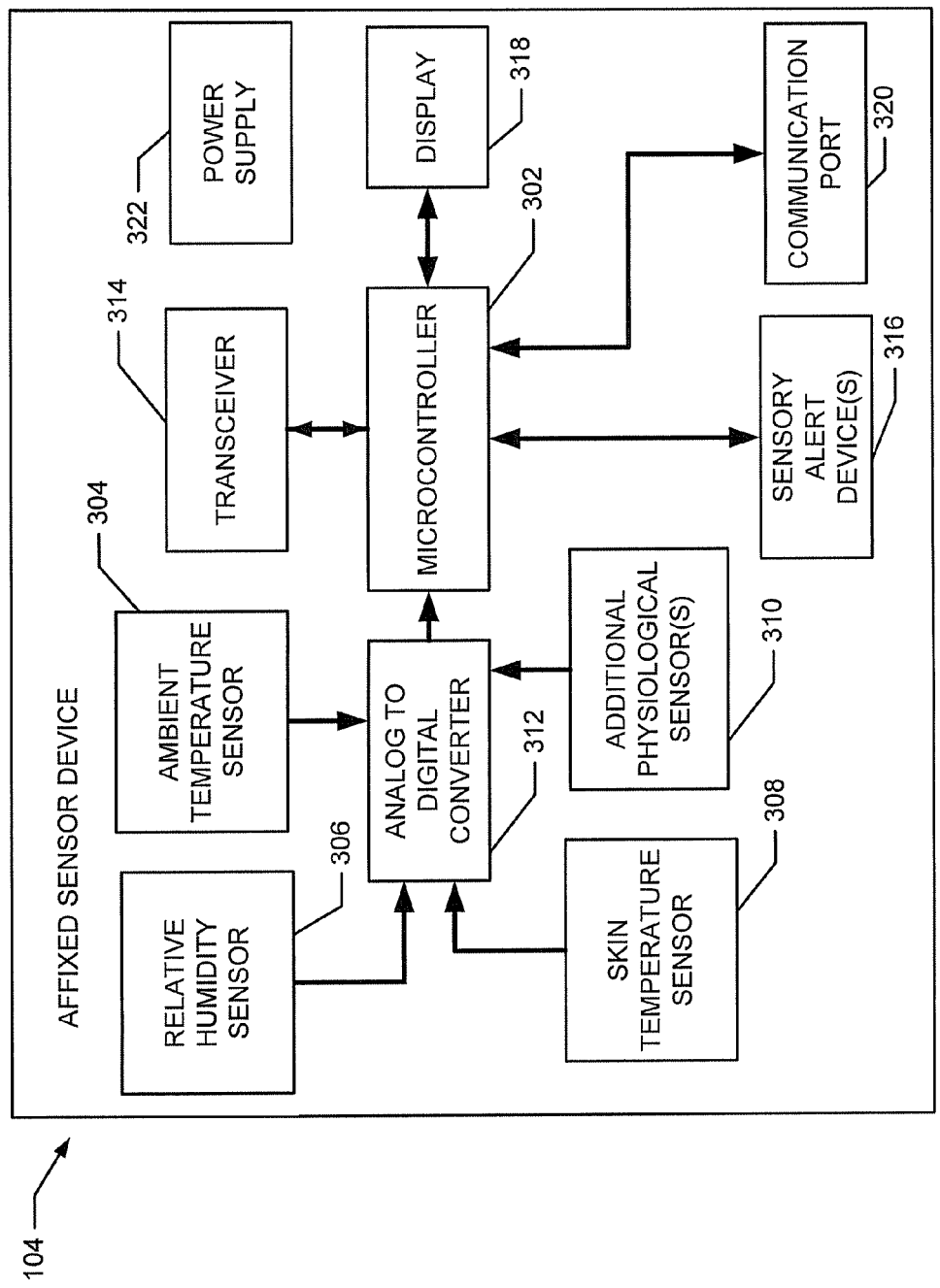
FIG. 3 is a block diagram showing the sub-components of an affixed sensor device.

FIG. 3 is a block diagram illustrating the sub-components of the affixed sensor device 104. The affixed sensor device 104 may include a microcontroller 302 that may contain stored instructions and one or more processors for implementing the various functions of the affixed sensor device 104 described in detail below.

The microcontroller 102 may receive and process sensor data from a variety of internal and external sensor sources to assess environmental and physiological conditions. Non-limiting examples of external sensor sources include the sensors of the monitor station 102 and the remote environmental sensor devices 106. These external sensor sources may communicate wirelessly with the affixed sensor device 104 via a transceiver 314.

The affixed sensor device 104 may include one or more internal environmental sensors, including, but not limited to, an ambient temperature sensor 304 and a relative humidity sensor 306 to monitor environmental conditions in the immediate vicinity of the animal. The affixed sensor device 104 may further include physiological sensors including, but not limited to, a non-invasive skin temperature sensor 308 and an additional physiological sensor 310 to monitor the animal's physiological condition. A detailed description of sensor designs suitable for use as a skin temperature sensor 308 is provided herein below in the description of a collar monitor embodiment of the affixed sensor device 104. Depending on particular type of internal sensors incorporated, an analog to digital converter 312 may be included to convert the output of the ambient temperature sensor 304, the relative humidity sensor 306, the skin temperature sensor 308 and the additional physiological sensor 310 into a format usable by the microcontroller 302. Alternatively, the microcontroller 202 may include internal analog to digital conversion capability.

Additional environmental sensors and physiological sensors may be included in the affixed sensor device 104 to enhance the assessment of the animal's environmental and physiological condition. Non-limiting examples of additional environmental sensors suitable for use in the affixed sensor device 104 include wind speed sensors, light sensors, carbon dioxide sensors, carbon monoxide sensors, ammonia sensors, smoke detectors, and motion detectors. Non-limiting examples of additional physiological sensors suitable for use in the affixed sensor device 104 include sensors to measure core temperature, heart rate, respiration rate, blood oxygenation, blood glucose levels, expired $CO_2$, skin galvanic response, neural activity, physical movement, and muscle activity.

In order to account for variability in sensor measurements due to the limitations of instrumentation design, and/or the spatial variation of physiological quantities such as skin temperature between different regions of the animal's body, redundant physiological and environmental sensors may be included in the affixed sensor device 104. The microcontroller 102 may process the sensor data from redundant sensors in order to determine a single physiological or environmental condition. Non-limiting examples of data analysis methods suitable for processing redundant sensor data include selecting the highest or lowest reading, selecting a signal with the lowest variability, calculating an average, calculating a weighted average, and any other known data analysis technique.

The affixed sensor device 104 may further include a sensory alert device 316 to produce a sensory alert signal to indicate to the user that a dangerous environmental or physiological condition has been detected. Non-limiting examples of suitable sensory alert signals include audible tones, visible light signals, alphanumeric displays, vibrations, and combinations thereof. The sensory alert signal may be triggered by a signal generated by the microcontroller 302 of the affixed sensor device 104, by a signal received from the monitor station 102 via the transceiver 314, or any combination thereof.

The microcontroller 302 may further include a display 318 to provide the user with an indication of the current environmental and or physiological conditions as assessed by the algorithms of the affixed sensor device 104 and/or monitor station 102. The display 318 may be substantially similar to the display 218 of the monitor station 102 described herein above. Non-limiting examples of suitable display devices include alphanumeric displays such as LED or LCD displays, color-coded lights, variable-height bar displays, dials, and any other suitable visual display known in the art.

A communication port 320 may also be included in the affixed sensor device 104 to provide a variety of interface functions including, but not limited to, programming or trouble-shooting the microprocessor 302, and uploading or downloading data and/or instructions to the microprocessor 302.

The affixed sensor device 104 may further include a power supply 322 to provide power to the subcomponents of the affixed sensor device 104. The power supply 322 may be a portable power supply because the affixed sensor device 104 typically travels with the animal. Non-limiting examples of devices suitable for use as a power supply 322 include single-use batteries, rechargeable batteries, and solar power units.

c. Remote Environmental Sensor Devices

Figure 13:
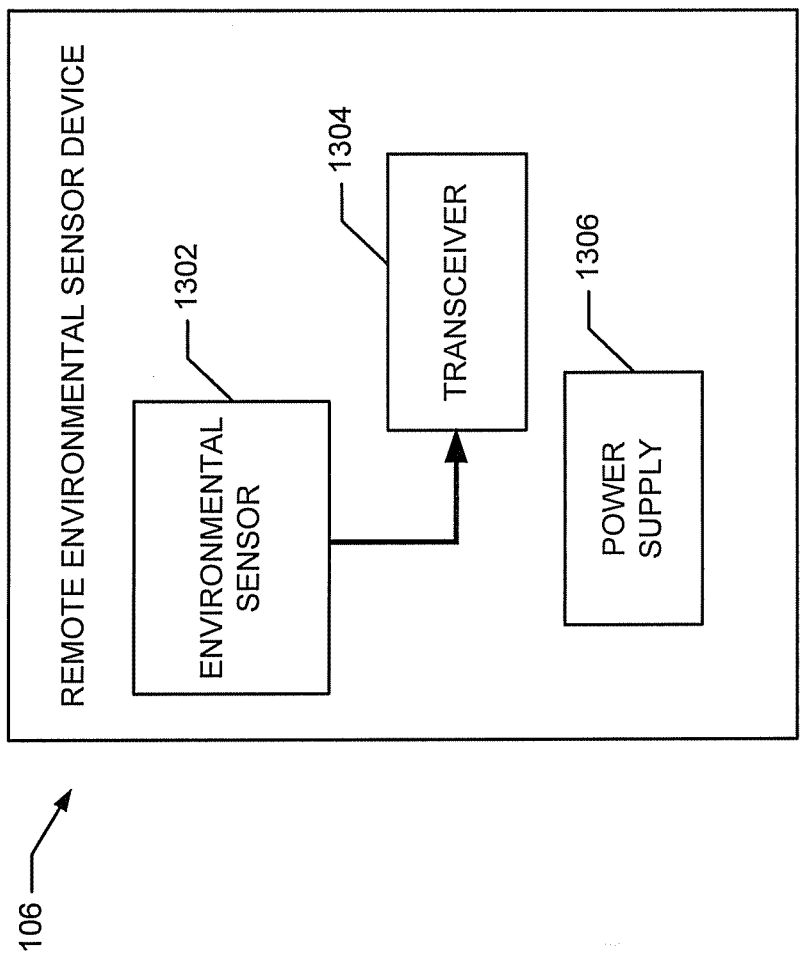
FIG. 13 is a block diagram showing the sub-components of a remote alert device.

The monitor system 100 may further include one or more remote environmental sensor devices 106. These remote environmental sensor devices 106 may be situated anywhere within the expected movement range of the animal or human to be monitored. FIG. 13 is a block diagram illustrating the subcomponents of a remote environmental sensor device 106 that includes one or more environmental sensors 1302 to measure a local environmental condition, a transceiver to transmit the sensor signal to other devices in the monitor system 100 including but not limited to the monitor station 102 and the affixed sensor device 104. Non-limiting examples of sensors suitable for use as environmental sensors 1302 include ambient temperature sensors, relative humidity sensors, wind speed sensors, light sensors, carbon dioxide sensors, carbon monoxide sensors, ammonia sensors, smoke detectors, and motion detectors. Non-limiting examples of suitable power sources for use as a power supply 1306 include single-use batteries, rechargeable batteries, batteries integrated into vehicles, solar power units, miniature wind-driven units, or other supplies of electrical power that may be incorporated in or connected to the monitor station 104. Because the one or more remote environmental sensor devices 106 may be situated in relatively inaccessible sites, a self-sustaining renewable power source, including but not limited to solar power units and miniature wind-driven units may reduce the need for maintenance tasks such as battery replacement.

d. Remote Alert Device

The remote alert device 108 may be used to monitor the animal in real time or to alert a user of dangerous environmental or physiological conditions. The remote alert device 108 may take any convenient and portable form, including, but not limited to, a key fob, a pager, a cellular phone, or any other known mobile monitoring device.

Figure 4:
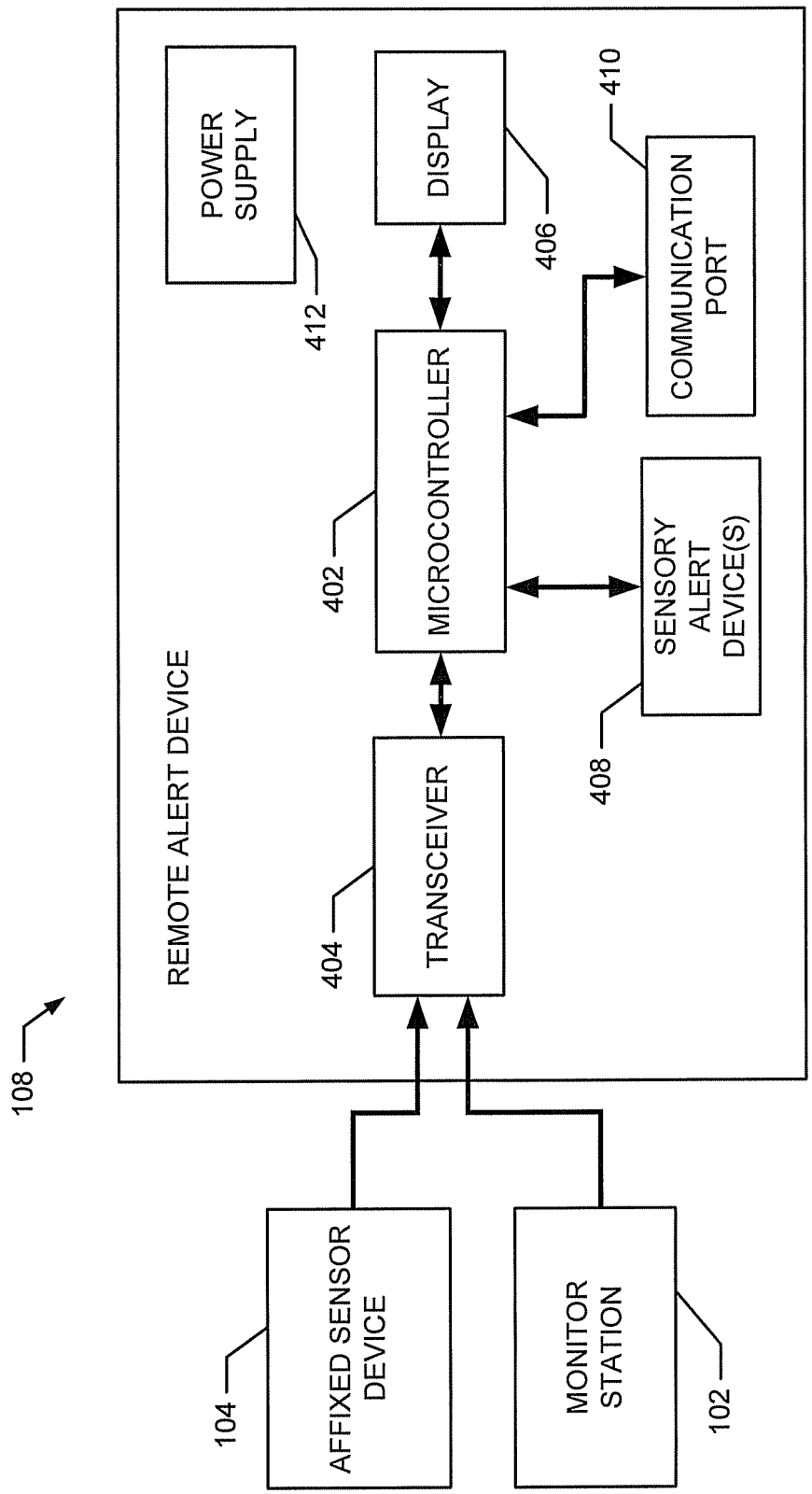
FIG. 4 is a block diagram showing the sub-components of a remote alert device.

FIG. 4 is a block diagram illustrating the subcomponents of a remote alert device 108. Although the remote alert device 108 may not itself include any sensors, the remote alert device 108 may maintain wireless communication with other devices of the monitor system 100 that do include sensors, including but not limited to the affixed sensor device 104 and the monitor station 102. This wireless communication may be accomplished by receiving signals from the other devices via a transceiver 404. A microcontroller 402 may process the signals received from the affixed sensor device 104 and/or monitor station 102 and issue a sensory alert signal to the user via a sensory alert device 408. Non-limiting examples of suitable sensory alert signals include audible tones, visible light signals, alphanumeric displays, vibrations, and combinations thereof. For example, the sensory alert signal may include the illumination of one or more light emitting diode indicators which may be different colors. The sensory alert signal may provide a quantitative indication of the level of danger such as an ambient temperature reading, a skin temperature reading, a heat index or a computed number.

The power supply 412 of the remote alert device 108 may be any known power source including, but not limited to single-use batteries, rechargeable batteries, batteries integrated into vehicles, solar power units, or other supplies of electrical power. Because the remote alert device 108 is typically carried with a user, a compact and lightweight power source such as a single use battery, a rechargeable battery, or a solar power unit may be used as a power supply 412.

Both the monitor station 102 and the remote alert device 108 may issue alerts to the user to communicate the detection of unsafe conditions to ensure that the user receives the alert regardless of the user's location relative to the monitor station 102. Alternatively, the remote alert device 108 may function as a standalone alert device monitor system 100. For example, a user may take a dog to the dog park but does not wish to bring along the larger monitor station 102. In the absence of the monitor station 102, the affixed sensor device 104 may communicate directly with the remote alert device 108 to inform the user of potentially dangerous conditions without need for the monitor station 102.

2. Collar Monitor

Figure 5:
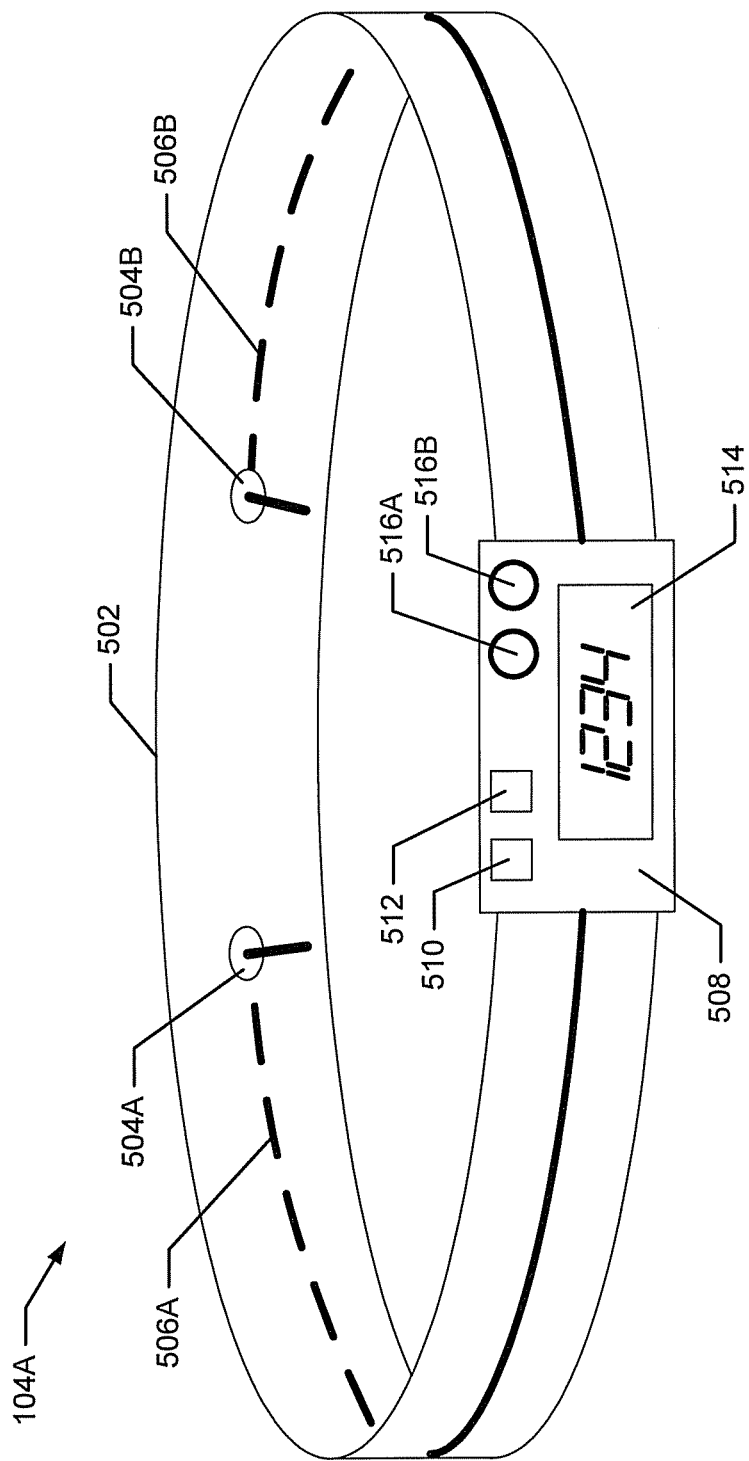
FIG. 5 is a schematic illustration of a collar-mounted affixed sensor device.

The affixed sensor device 104 of the monitor system 100 may take the form of a collar monitor 104A, illustrated schematically in FIG. 5. The collar monitor 104A may be affixed to any suitable animal, including but not limited to humans, working animals such as military dogs and assist animals, companion animals such as dogs and cats, and livestock such as cattle, pigs, and chickens. Depending on the animal and context of use, the collar monitor 104A may be affixed to any known appendage including but limited to an arm, a leg, a neck, a head, a finger, a toe, and any combination thereof.

The collar monitor 104A may include a collar 502 that serves as the substrate for the fixation of collar monitor 104A to the animal. In addition, the collar 502 may further function as a substrate to which the other components of the collar monitor 104A may be fixedly mounted. The collar 502 may be secured around the appendage of the animal using any known collar fastening mechanism including, but not limited to buckles, clasps, snaps, hooks, Velcro, or any other known collar fastening mechanism. The collar material may be selected on any one or more of at least several factors, including, but not limited to, strength and durability to remain attached to the animal in its working environment, suitable stiffness or strength to retain attached components of the collar monitor 104A in use, non-interference with the function of the electrical components of the collar monitor 104A, and biocompatibility with the animal. Non-limiting examples of suitable collar materials include leather, cotton, woven nylon and other polymers.

One or more skin temperature sensors 504A and 504B may be mounted on the collar 502 such that the sensor tips protrude from the collar 502 such that the sensor tips penetrate the fur of the animal to make contact with the animal's skin when the collar monitor 104A is fastened to the animal. For example, two or more skin temperature sensors 504 may be included in the collar monitor 104A to provide redundant measurements to account for regional skin variations, and to provide continuous skin temperature readings in the case of a sensor failure.

The skin temperature sensors 504A and 504B may be electrically connected to wire harnesses 506A and 506B, respectively. The wire harnesses 506A and 506B supply electrical power to the skin temperature sensors 504A and 504B and conduct sensor signals to the microprocessor (not shown) situated inside the collar housing 508. The wire harnesses 506A and 506B may be situated on the surface of the collar material or the wire harnesses 506A and 506B may be embedded within the interior of the collar 502.

The collar housing 508 contains the remaining electrical components of the collar monitor 104A. In addition, the collar housing may include an aperture 510 through which an ambient temperature sensor (not shown) may obtain temperature readings. A second aperture 512 may be included in the collar housing 508 through which a relative humidity sensor (not shown) may obtain readings. A display 514, also included in the collar housing, may display user information such as the status of the collar monitor 104A, measured environmental or physiological conditions, alerts to indicate dangerous conditions, or any combination thereof. Although an alphanumeric display 514 is illustrated in FIG. 5, the display may be any other known display type including but not limited to colored light signals, bar graphs, and any other known display.

The collar housing 508 may further include one or more buttons 516A and 516B to provide a user interface to the collar monitor 104A. For example, the one or more buttons 516A and 516B may be used to indicate the desired temperature units for the display 514, to set a threshold temperature at which an alert should be issued, to change the format of the display 514, to switch the display between individual sensors, and to put the collar monitor 104A into a sleep mode to conserve power.

The collar housing 508 may be designed to be lightweight and compact to minimize the effects of the collar monitor 104A on the movements of the animal. The collar housing 508 may further include seals, coatings or any other known means of sealing the electrical components from moisture, dust, and other harmful environmental factors. The material from which the collar housing 508 may be selected based on any one or more of at least several factors, including, but not limited to toughness in the operating environment, moisture and dust resistance, biocompatibility with the animal, and non-interference with the electrical components of the collar monitor 104A. Non-limiting examples of suitable housing materials include metals and plastics.

Figure 6:
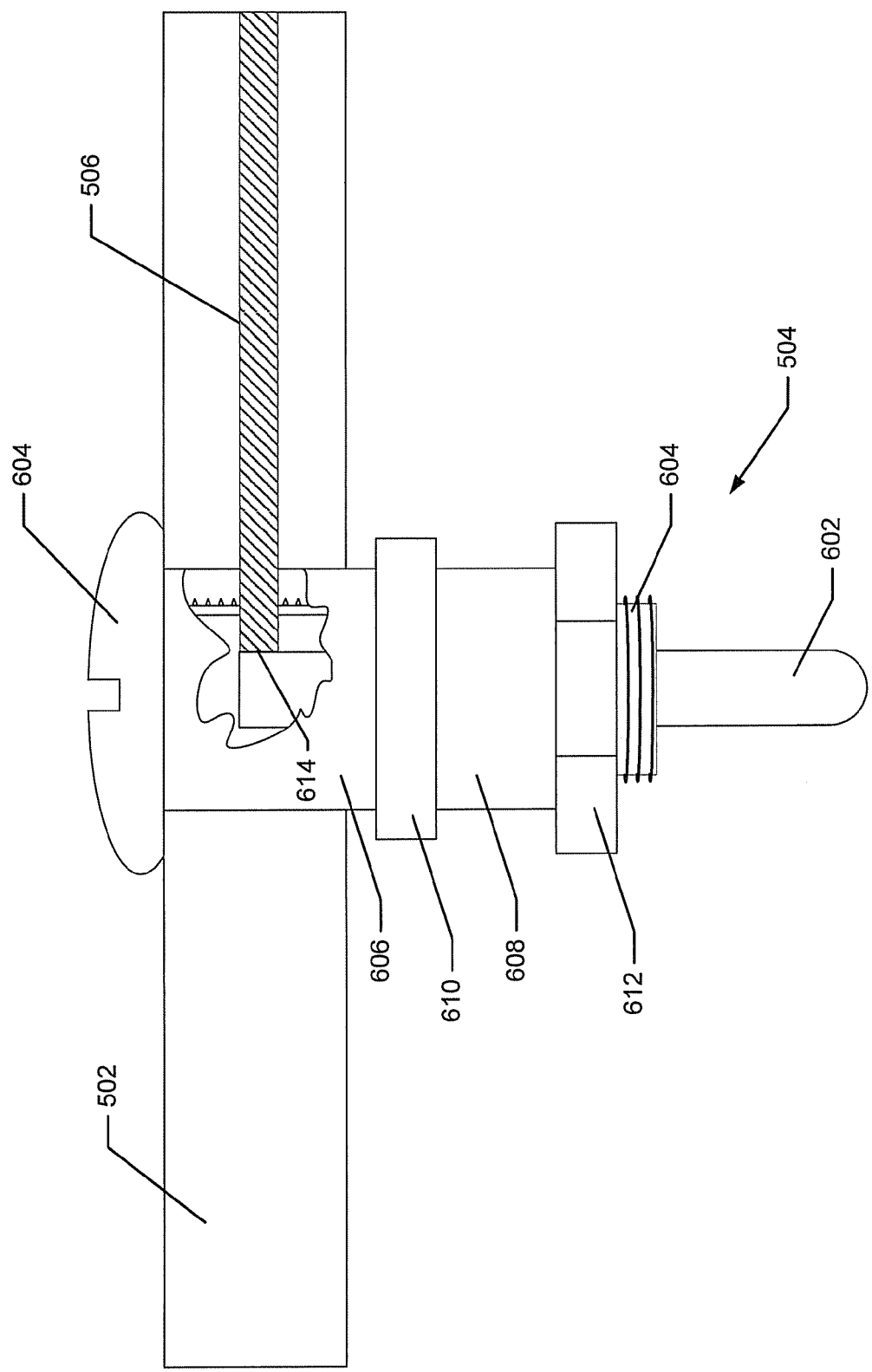
FIG. 6 is a cut-away view of a temperature sensor affixed to the collar of a collar-mounted affixed sensor device using a rigid attachment.

FIG. 6 is a schematic illustration of a rigid attachment of a skin temperature sensor 504 to the collar 502. A hollow cylinder 606 may be inserted through the material of the collar 502 from the outer surface 614 to the inner surface 616, forming a channel. A hollow screw 604 may be inserted through the hollow cylinder 606 such that the threaded shaft 605 protrudes inward from the inner surface 616 of the collar. A skin temperature probe 602 may be inserted upwards into the lumen of the hollow screw 604 and the wire harness 506 may be inserted through an aperture 607 leading to the lumen of the hollow screw. Inside the lumen, the harness 506 may be attached to the skin temperature probe 602 with an electrical connection 614. A second hollow cylinder 608 and a rubber grommet 610 may be placed over the threaded end 605 of the hollow screw 604 such that the rubber grommet 610 is situated between the first hollow cylinder 606 and the second hollow cylinder 608. A threaded nut 612 may be twisted onto the end of the threaded shaft 605 until the rubber grommet 610 is compressed between the first hollow cylinder 606 and the second hollow cylinder 608.

Figure 7:
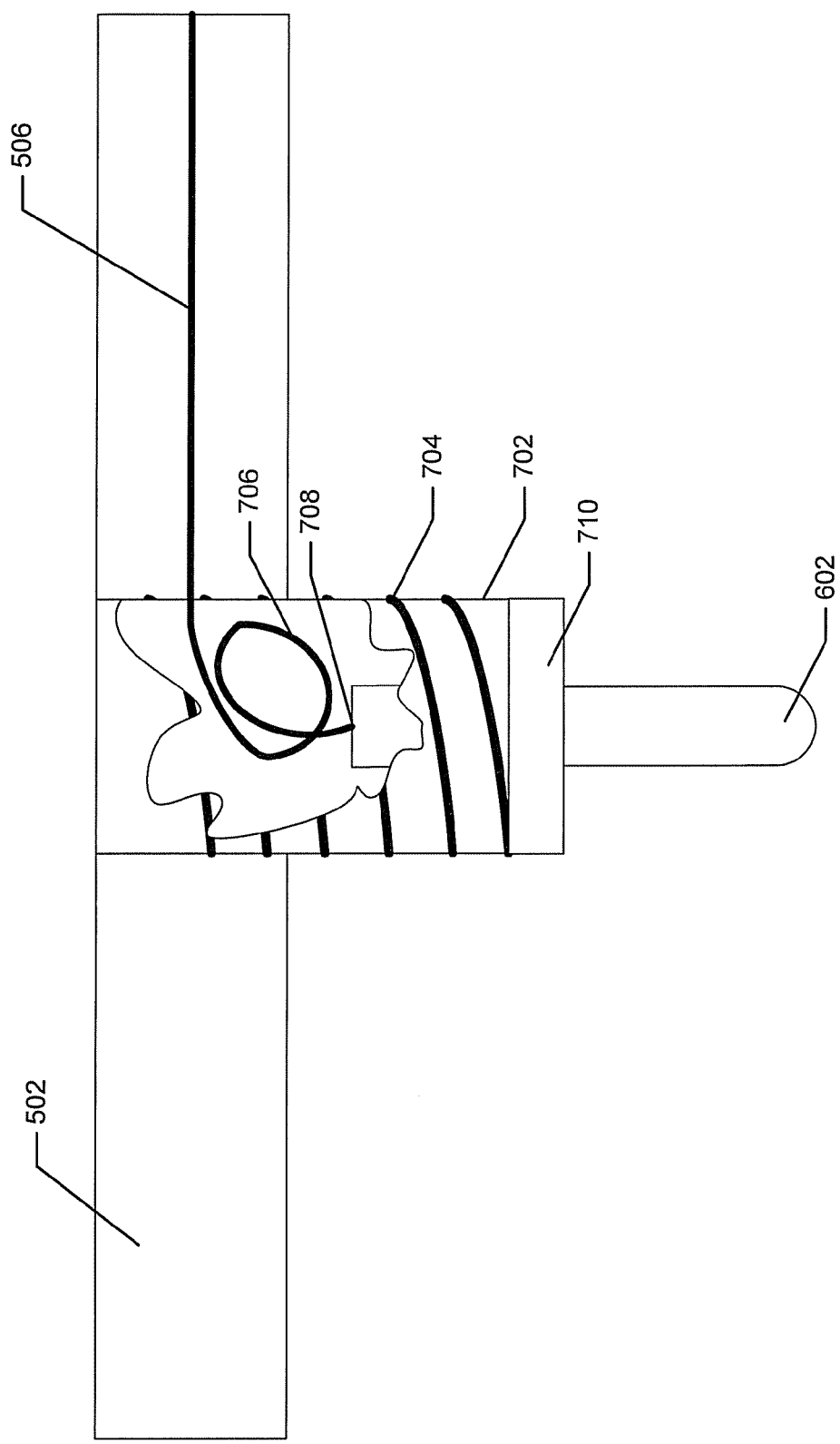
FIG. 7 is a cut-away view of a temperature sensor affixed to the collar of a collar-mounted affixed sensor device using a flexible attachment.

FIG. 7 is an illustration of a flexible attachment of a skin temperature sensor 504 to the collar 502. The flexible attachment may include a flexible cylinder 702 attached to the collar 502. The flexible cylinder 702 may be made of any known flexible, fatigue-resistant material including but not limited to rubber and any other known flexible polymer. To provide additional structural integrity, the flexible cylinder 702 may be reinforced by a helical spring 702 constructed of a more rigid material including, but not limited to a metal or a rigid thermoplastic material. A skin temperature probe 602 may be inserted upwards into the lumen of the flexible cylinder 702. The wire harness 506 may be inserted through the wall of the flexible cylinder 702 into the lumen and attached to the skin temperature probe 602 in an electrical connection 708. A flexible loop 706 of wire harness 506 may be maintained inside of the lumen of the flexible cylinder 702 to provide a flexible and fatigue-resistant electrical connection 708. The end of the skin temperature probe 602 may protrude through an end cap 710, which is secured to the free end of the flexible cylinder 702.

In use, the protruding ends of the skin temperature probes will contact the skin of the animal once the collar monitor 104A is secured to an appendage of the animal. The skin temperature probes will measure surface skin temperature and this information will be processed within the microprocessor of the collar monitor 104A situated in the collar's housing 508 and remotely transmitted to a monitor station 102 and/or a remote alert device 108. When the skin temperature reaches a research-based pre-determined, pre-programmed critical level, the collar monitor 104A and/or the monitor station 102 may issue an alert to the user. Additionally, the collar monitor 104A will measure the localized heat index (i.e. a combined temperature/humidity measure) of the air surrounding the animal at the level of the animal's appendage. The localized heat index information may be processed within the collar monitor 104A and remotely transmitted to the monitor station 102 and/or the remote alert device 108. When the heat index reaches a research-based pre-determined, pre-programmed critical level, the collar monitor 104A may issue an alert to the user.

Alert signals produced by the collar monitor 104A and triggered when skin temperature and/or heat index reaches critical levels may function as a failsafe mode if the transmission of information to the other components of the monitor system fails. The collar monitor 104A may also be used as a standalone product for animals at risk for hyperthermia in other circumstances, such as military dogs in extreme operational environments.

3. Monitoring Method

The monitor system software receives and processes the sensor signals originating from an array of sensor devices, processes a selected combination of sensor signals to monitor the environmental and physiological condition of an animal, and issues an alert if the sensor signals indicate a dangerous condition. The monitor system software instructions and modules may be stored in computer readable media on any one of more devices of the monitor system 100, including, but not limited to the monitor station 102 and the affixed sensor device 104.

Computer readable media may include volatile media, nonvolatile media, removable media, non-removable media, and/or another available medium that can be accessed by a computing device, such as a microprocessor. By way of example and not limitation, computer readable media comprise computer storage media and communication media. Computer storage media includes memory, volatile media, nonvolatile media, removable media, and/or non-removable media implemented in a method or technology for storage of information, such as computer readable instructions, data structures, program modules, or other data. Communication media may embody computer readable instructions, data structures, program modules, or other data and include an information delivery media or system.

Figure 8:
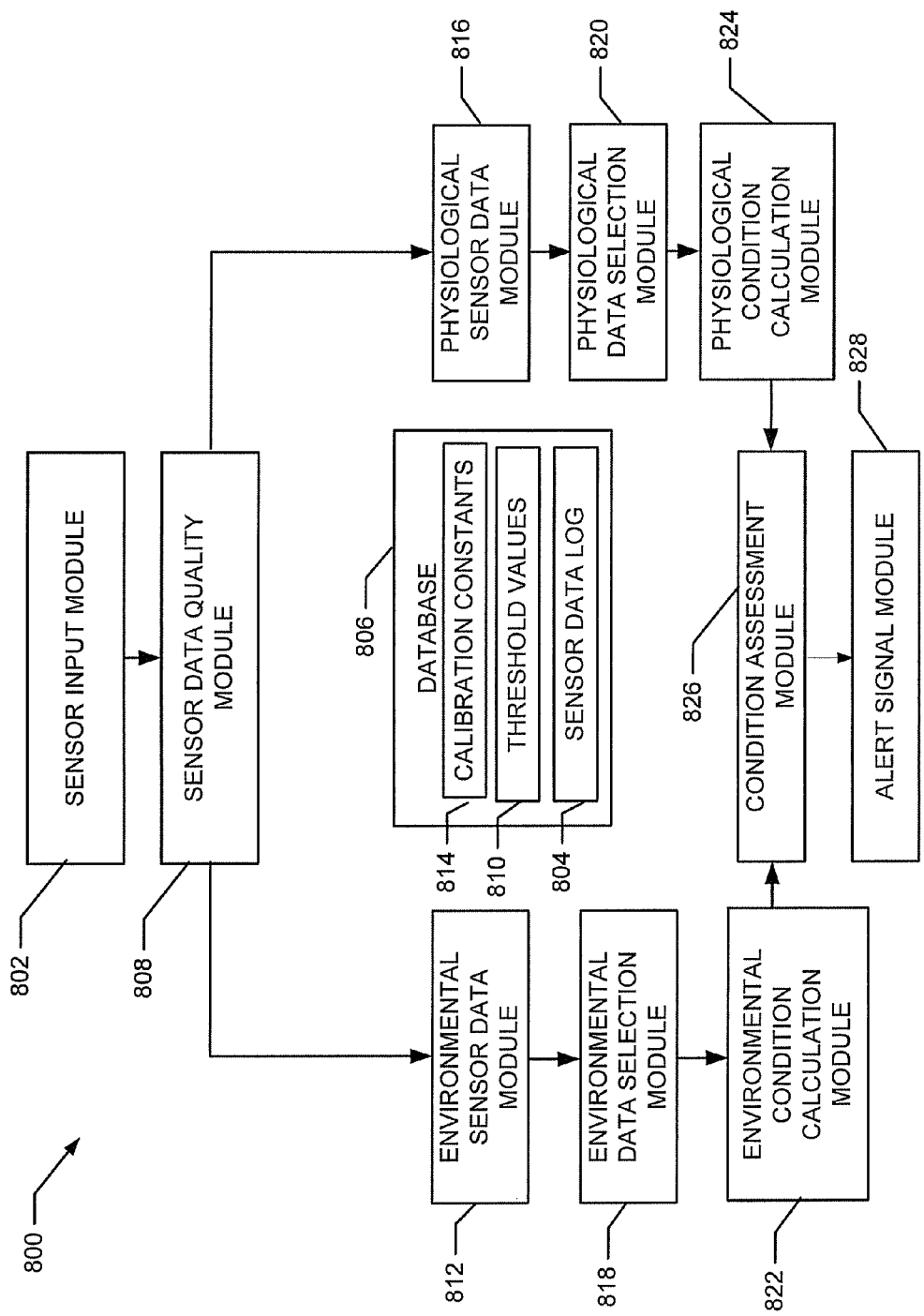
FIG. 8 is block diagram illustrating the modules of a monitor software system for a monitor system.

FIG. 8 is a flow chart illustrating a computer readable medium 801 containing the stored modules and database of a monitor software system 800. The sensor input module 802 receives sensor data from any one or more of the sensor devices included in the monitor station 102, affixed sensor device 104, and/or one or more remote environmental sensors 106 of the monitor system 100. Because the sensor data either originates from internal sensors or may be received via wireless transmissions from other devices of the monitor system 100, the sensor input module 802 may receive the sensor data in a multiplexed fashion. The sensor input module 802 may identify the particular device from which a particular sensor signal may have originated as well as the specific type of sensor (i.e. ambient temperature, relative humidity, etc.). In addition, the sensor input module 802 may generate a continuous log of all sensor data received from each sensor and may store the continuous log in a sensor data log 804 on a database 806 stored on computer readable media.

The sensor data quality module 808 may process the sensor data received from the sensor input module 802 to determine whether the sensor data is of sufficient quality for the assessment of environmental or physiological conditions. For example, the sensor data quality module 808 may select a particular sensor signal for processing if the sensor signal has a signal magnitude that falls above a minimum magnitude threshold and below a maximum magnitude threshold. The minimum and maximum magnitude thresholds may be stored as entries among a set of threshold values 810 stored on the database 806. As another example, the sensor data quality module 808 may select a particular sensor signal for processing if the sensor signal is received at a signal rate that is higher than a threshold signal rate (i.e. the sensor signal has no significant dropouts) or if the sensor signal has a variance that falls below a threshold variance. The sensor data quality module 808 may select a particular sensor's data based on a statistical analysis of multiple sensor signals. The sensor data quality module 808 may reject outlier sensor signal data or otherwise validate the proper operation of sensors and only incorporate the data from those sensors that are determined to be operating properly. All threshold values 810 are stored in the database 806.

Figure 14:
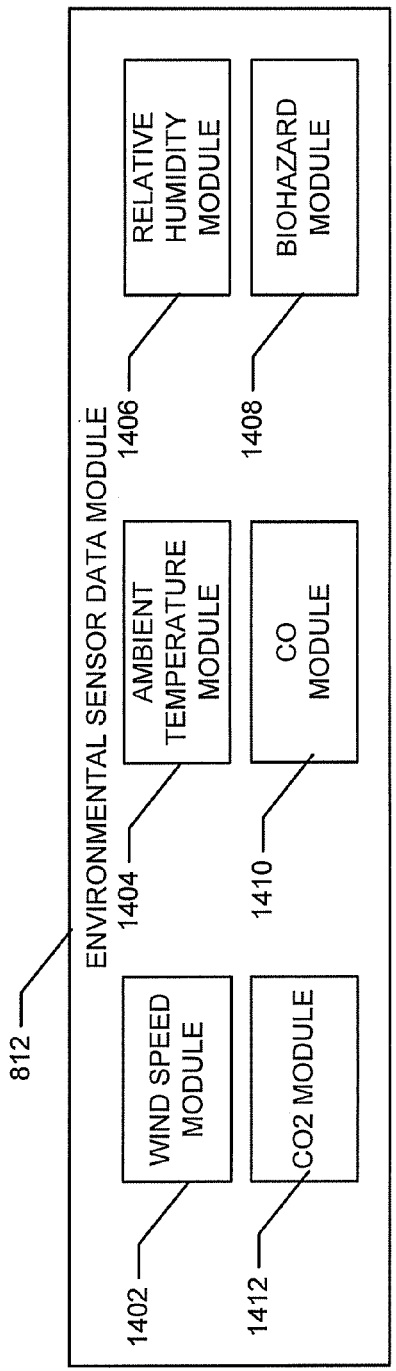
FIG. 14 is a block diagram showing the sub-components of an environmental sensor data module.

The environmental sensor signals such as ambient temperature and relative humidity that are selected for additional processing by the sensor data quality module 808 are received and processed by the environmental sensor data module 812. As received, the environmental sensor data is in the form of a voltage generated by the sensor. The environmental sensor module data module 812 transforms the sensor voltage signals into measured environmental conditions using a calibration equation unique to each particular sensor. FIG. 14 is a block diagram showing examples of particular modules 1402-1412 used to generate the measured environmental conditions. For example, the ambient temperature module 1404 may transform the received ambient temperature voltage signal into an ambient temperature measurement using a calibration equation for the ambient temperature sensor. The calibration constants for the calibration equations used in each of the modules 1402-1412 are retrieved from calibration constants 814 stored in the database 806.

Figure 15:
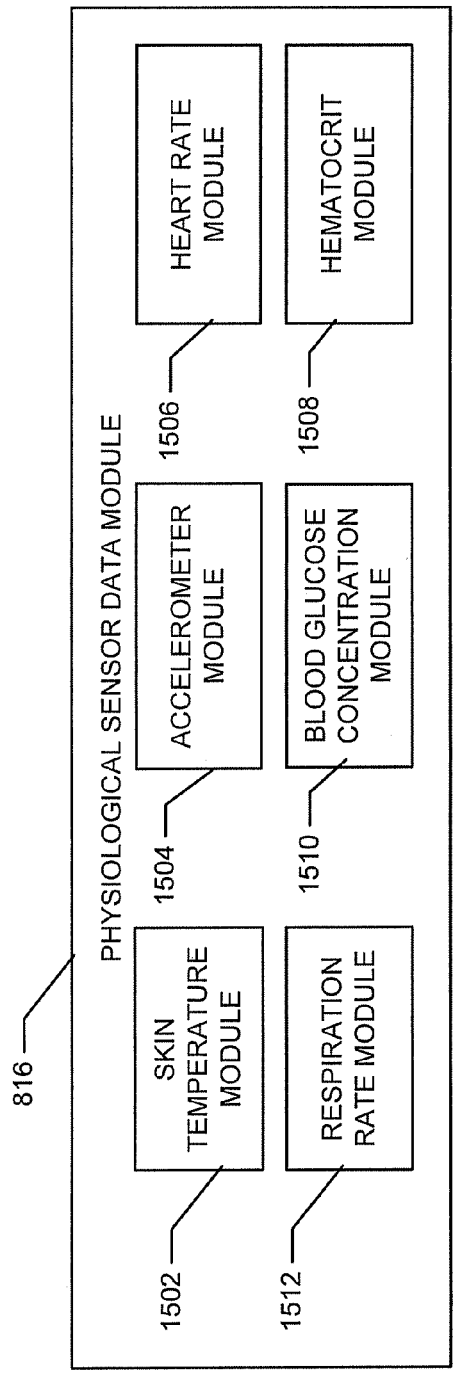
FIG. 15 is a block diagram showing the sub-components of a physiological sensor data module.

Similarly, the physiological sensor voltage signals are received by the physiological sensor data module 816, as illustrated in FIG. 15. Examples of individual sensor modules 1502-1512 are shown in FIG. 15. For example, the skin temperature module 1502 may convert skin temperature voltage signals into skin temperatures using a calibration equation that incorporates sensor calibration constants 814 retrieved from the database 806.

The environmental data selection module 818 and the physiological data selection module 820 assess the measurements received from the environmental sensor data module 812 and the physiological sensor data module 816, respectively. The data selection modules 820 and 812 may eliminate redundant measurements by a variety of methods, including but not limited to selecting the minimum or maximum redundant measurement, selecting a median redundant measurement, and selecting an average of the redundant measurements. In addition, the data selection modules 820 and 812 assess what measurements are available or unavailable for processing by the condition assessment module.

Figure 16:
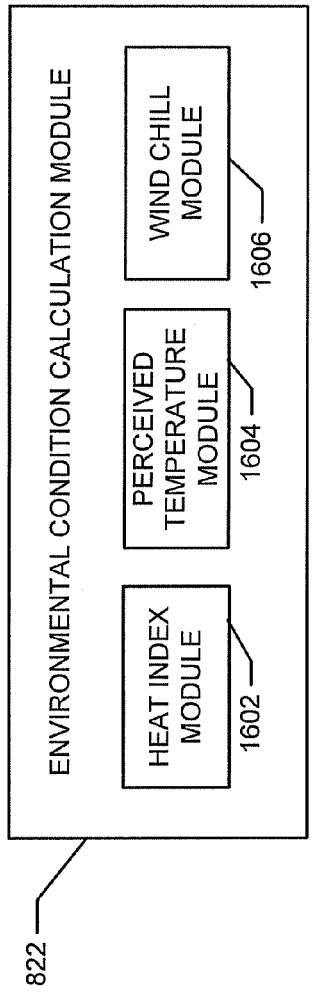
FIG. 16 is a block diagram showing the sub-components of an environmental condition calculation module.

The environmental condition calculation module 822 processes the environmental measurements and calculates one or more environmental conditions including but not limited to heat index, perceived temperature, or wind chill. Examples of the modules of the environmental condition calculation module 822 are illustrated in FIG. 16. The heat index module 1602 may calculate a heat index value by combining the ambient temperature and relative humidity measurements using known heat index equations. The perceived temperature module 1604 may calculate a perceived temperature value by combining the ambient temperature, relative humidity, and wind speed measurements using known perceived temperature equations. The wind chill module 1606 may calculate a wind chill value by combining the ambient temperature and wind speed measurements using known wind chill equations.

Figure 17:
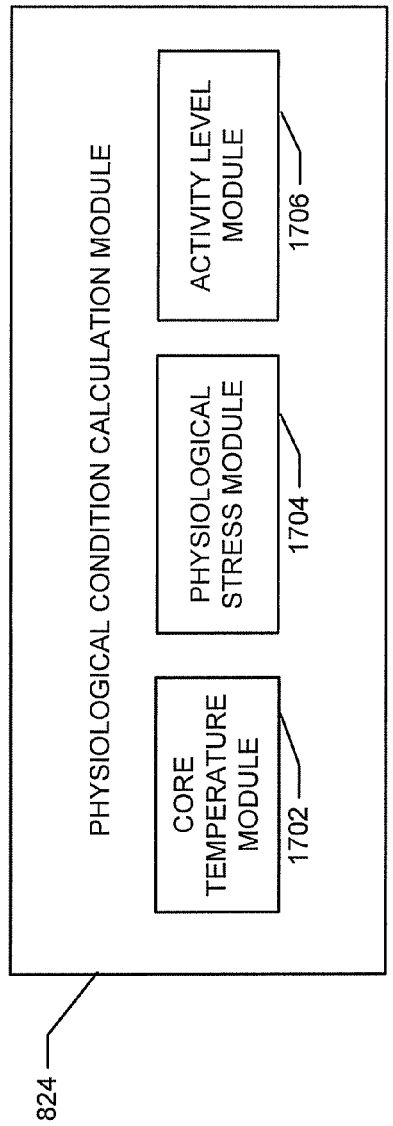
FIG. 17 is a block diagram showing the sub-components of a physiological condition calculation module.

The physiological condition calculation module 822 processes the physiological measurements and calculates one or more physiological conditions including but not limited to core temperature, physiological stress, or activity level. Examples of the modules of the physiological condition calculation module 822 are illustrated in FIG. 17. For example, the core temperature module 1702 may calculate a core temperature by combining physiological measurements such as the skin surface temperature and accelerometer-based assessments of animal activity. The relationship between the physiological measurements and core temperature may vary significantly depending on a variety of factors including, but not limited to, the physiological measurements and the species of the animal to be assessed. For example, the relationship between the physiological measurements and core temperature may be an empirically-derived relationship based on previously obtained experimental data. This relationship between physiological measurements a core temperature may be implemented as a core temperature rule. By substituting the physiological measurements such as skin temperature and animal activity into the core temperature rule, a core temperature may be calculated. The core temperature rule may be empirically derived and may vary by animal age, weight, sex, and/or any other physiologically relevant classification.

The physiological stress module 1704 may calculate a physiological stress index by combining selected physiological measurements including, but not limited to core temperature, heart rate, and blood oxygenation in an empirically-derived equation. The relationship between the physiological stress index and the physiological measurements may be implemented as a physiological stress rule to calculate physiological stress. For example, the physiological stress rule may be a table of physiological stress index values as a function of core temperature, heart rate, and other physiological measurements. The physiological stress rule may be empirically derived and may vary by animal age, weight, sex, and/or any other physiologically relevant classification.

The activity level module 1706 may calculate an activity level that quantifies the degree of active behavior by assessing accelerometer data, trends in respiration rate or heart rate, or any other physiological measurements using an empirically-derived relationship and/or an animal activity rule. For example, an animal activity rule may define the animal activity level as active if the accelerometer reading falls above a predetermined maximum non-active animal accelerometer reading. This animal activity rule may define the animal activity level as inactive if the accelerometer reading falls at or below a predetermined maximum non-active animal accelerometer reading. The animal activity rule may be empirically derived and may vary by animal age, weight, sex, and/or any other physiologically relevant classification.

Referring back to FIG. 8, the condition assessment module 826 processes the calculated physiological and environmental conditions and assesses whether or not a dangerous condition exists. If a dangerous condition is identified by the condition assessment module 826, the alert signal module 828 issues an alert signal to the devices of the monitor system 100. The condition assessment module 826 may assess the conditions based on a variety of different criteria and algorithms.

Figure 9:
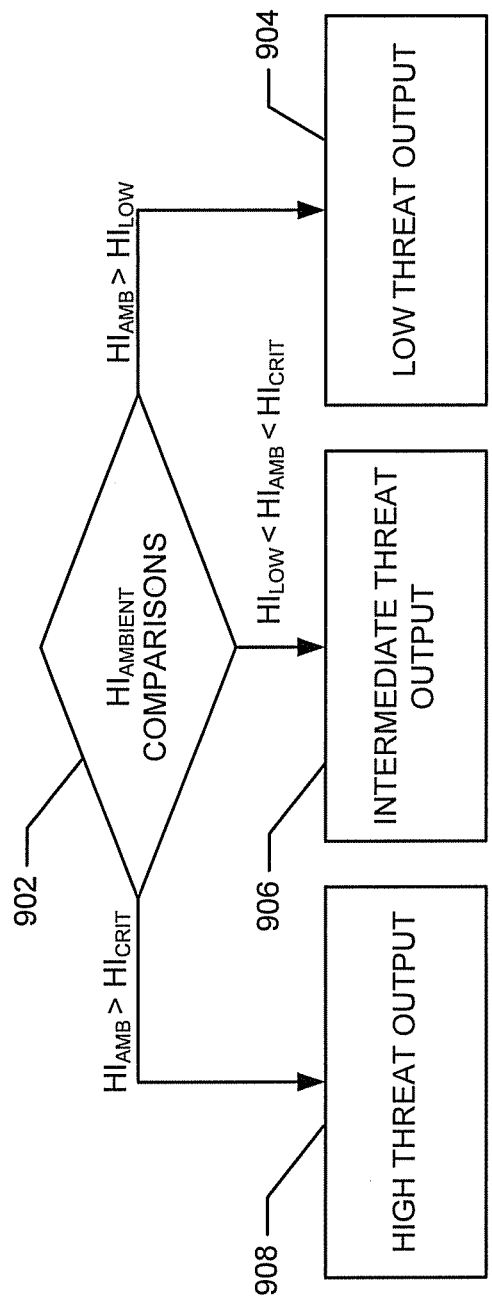
FIG. 9 is a flow chart illustrating an algorithm of a heat index-based condition assessment module.

FIG. 9 is a flowchart illustrating an algorithm that may be used to assess conditions based on the calculated heat index condition ($HI_{amb}$). The heat index maybe calculated by substituting the ambient temperature and the relative humidity into a heat index rule. The heat index rule may be any known equation or relationship that calculates the heat index as a function of the ambient temperature and the relative humidity. For example, the heat index may be retrieved from a standard table of heat index values as a function of ambient temperature and relative humidity.

The calculated heat index may be compared to a threshold dangerous heat index condition ($HI_{crit}$) and a threshold intermediate heat index condition ($HI_{low}$) at step 902. If the heat index is less than the threshold intermediate heat index condition ($HI_{low}$), a low threat condition is declared at step 904. If the heat index is greater than the threshold intermediate heat index condition ($HI_{low}$), but less than the threshold dangerous heat index condition ($HI_{crit}$), an intermediate threat condition is declared at step 906. If the heat index is greater than the threshold dangerous heat index condition ($HI_{crit}$), a high threat condition is declared at step 908.

Figure 10:
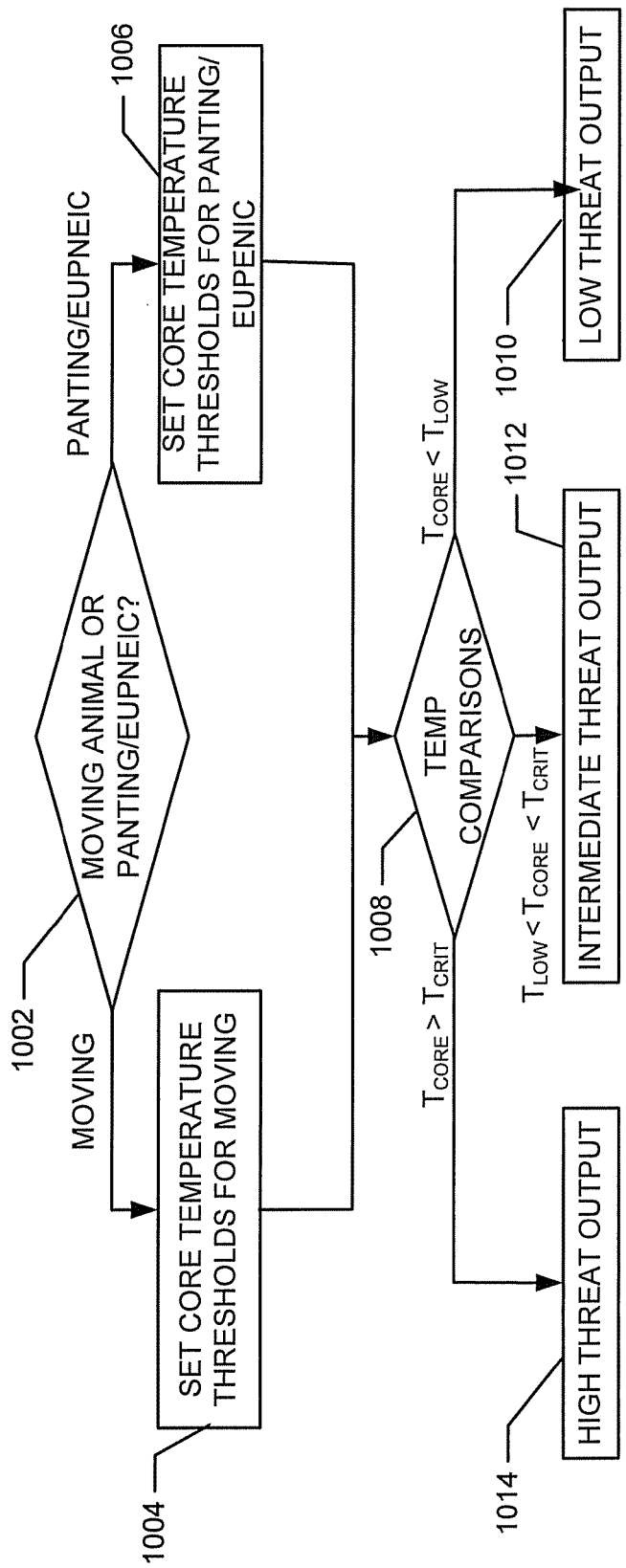
FIG. 10 is a flow chart illustrating an algorithm for a temperature and movement-based condition assessment module.

FIG. 10 is a flowchart illustrating another algorithm that may be used to assess conditions based on activity level and core temperature. The calculated activity level of the animal is processed to determine whether the animal is active (i.e. moving) or inactive (i.e. panting/eupneic) at step 1002. If the animal is determined to be moving based on the calculated activity level, a maximum core temperature threshold ($T_{crit}$) and an intermediate core temperature threshold ($T_{low}$) corresponding to the appropriate values for a moving animal are retrieved from the stored threshold values 810 in the database 806 at step 1004. If the animal is determined to be inactive (panting) based on the calculated activity level, a critical core temperature threshold ($T_{crit}$) and an intermediate core temperature threshold ($T_{low}$) corresponding to the appropriate values for a panting animal are retrieved from the stored threshold values 810 in the database 806 at step 1006. The calculated core temperature may be compared to the threshold values at step 1008. If the core temperature is less than the intermediate core temperature threshold ($T_{low}$), a low threat condition is declared at step 1010. If the core temperature is greater than the intermediate core temperature threshold ($T_{low}$), but less than the maximum core temperature threshold ($T_{crit}$), an intermediate threat condition is declared at step 1012. If the core temperature is greater than the critical core temperature threshold ($T_{crit}$), a high threat condition is declared at step 1014.

All devices and methods described herein may incorporate digital and/or analog signal processing to implement the functions of the monitor system. For example, a monitor system may include analog thresholding circuits in place of digital processors to process the sensor signals and determine the condition of the animal in the extreme environment. In this analog implementation, analog signals from the at least one physiological sensor and from the at least one environmental sensor may be combined using analog circuit techniques and the resulting analog output signal may be compared to a threshold value that may be pre-set on a potentiometer.

4. Methods of Monitoring an Animal's Condition in an Extreme Environment

The monitor system 100 may be used in various configurations to monitor the condition of a wide variety of animals in a wide variety of extreme environments. Several illustrative examples are provided herein below.

a. Dog Confined to Automotive Vehicle

For example, the monitor system may be used to monitor the condition of a dog confined to the passenger compartment of an automotive vehicle. In this example, the monitor station 102 may be placed in the passenger compartment with the dog. In this example, the environmental sensors of the monitor station 102 (i.e. the ambient temperature sensor 204 and relative humidity sensor 206) would continuously assess the heat index within the vehicle. If the heat index increased past an alert threshold, the monitor station would produce an alarm signal. For example, the alarm signal could take the form of a loud audible tone to alert the dog's owner, or the alarm signal could take the form of a text message sent to the owner's cellular phone. A remote alert device 108 may be added to the monitor system 108 to provide an additional alert to the dog owner.

In this example, additional remote environmental sensors 106 may be added to the monitor system to provide additional or redundant sensor data to be processed by the monitor station 102, or an affixed sensor device 104 in the form of a collar monitor 104A may be included in the monitor system 100 to provide additional environmental sensors as well as physiological sensors (i.e. skin temperature sensor 308).

In another example, a dog confined to the passenger compartment of an automotive vehicle may be outfitted with a collar monitor 104A. The collar monitor 104A includes environmental and physiological sensors to continuously monitor the condition of the dog in the vehicle. The collar monitor 104A may send an alert signal to a cellular telephone, to a remote alert device 108, or may produce a loud audible tone to alert the dog owner of a dangerous condition in the vehicle.

b. Soldier and Military Dog in Extreme Operational Environment

Figure 11:
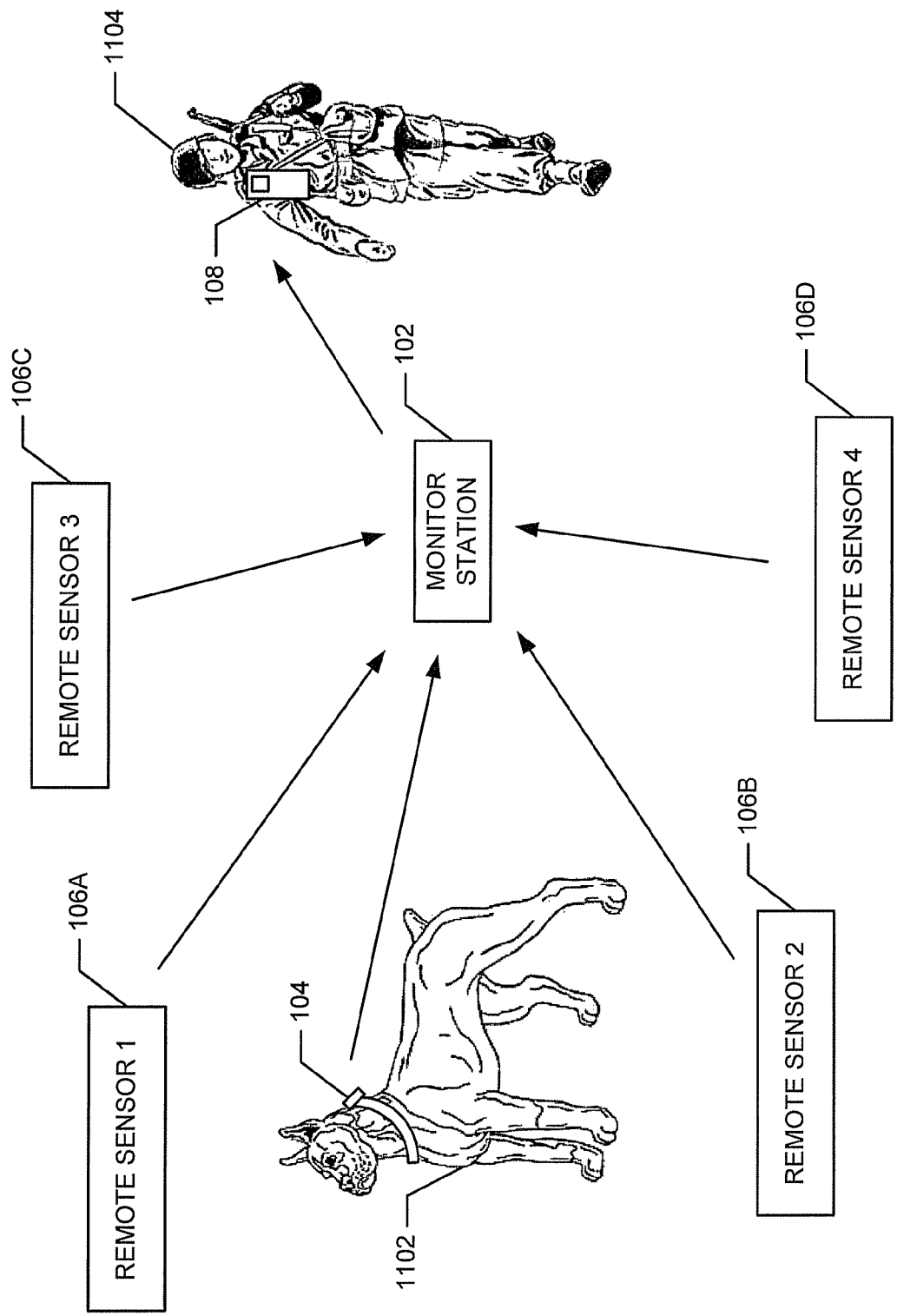
FIG. 11 is a schematic illustration of a monitor system as used by a working animal and trainer.
Figure 12:
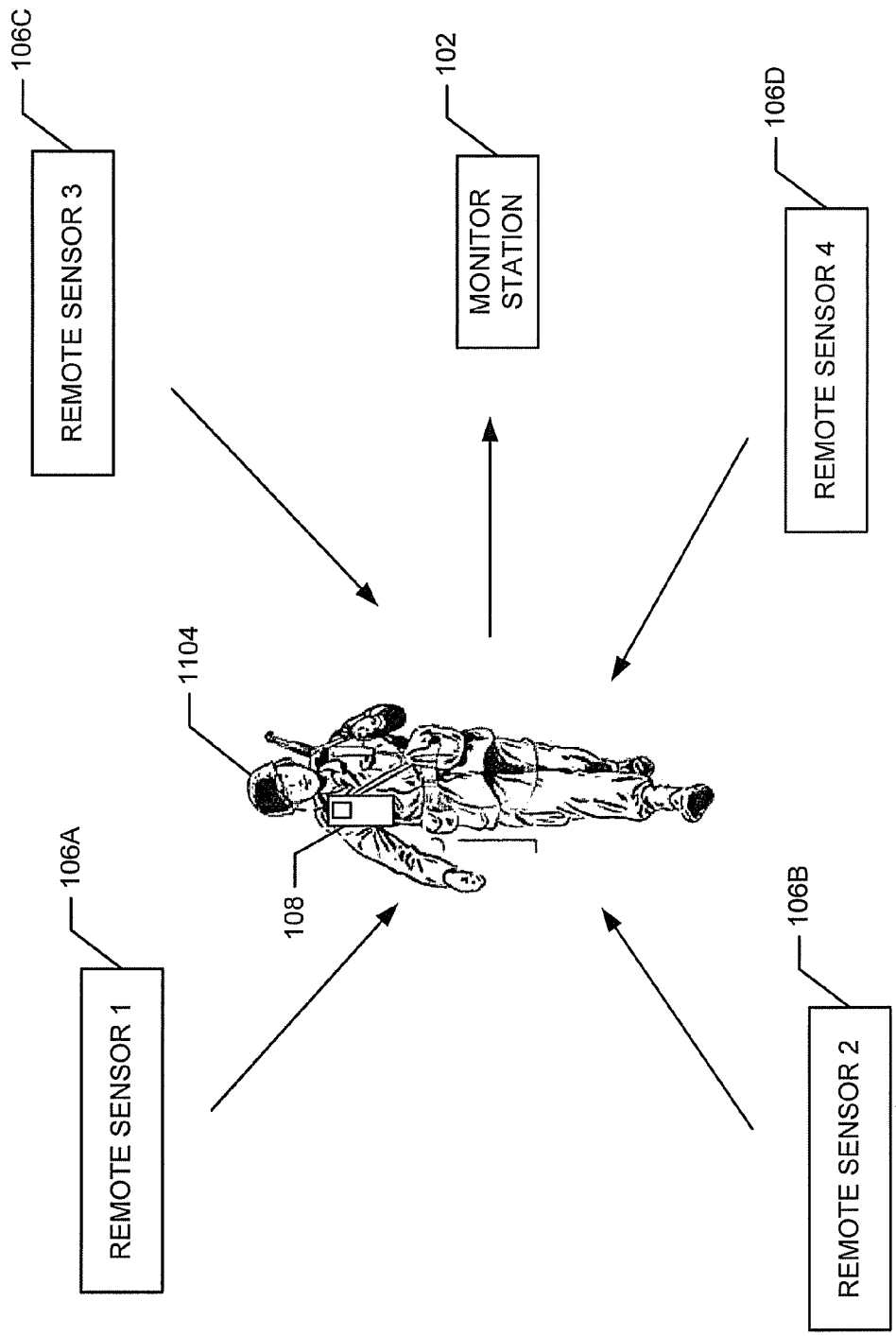
FIG. 12 is a schematic illustration of a monitor system as used by a human subject.

As illustrated in FIG. 11, the monitor system 100 may be used to monitor the condition of a military dog 1102 and report any dangerous conditions to a soldier 1104 as the soldier 1104 and dog 1102 move through an extreme operational environment. The dog 1102 may be outfitted with a monitor collar 104 that transmits environmental and physiological sensor data to a monitor station 102. In addition, the monitor station 102 may receive additional environmental data from additional remote sensors 106A, 106B, 106C, and 106D. The remote sensors may measure redundant environmental data and/or additional environmental data not measured by the collar monitor 104. For example, the collar monitor 104 may measure ambient temperature, relative humidity, and the dog's skin temperature. In addition, remote sensor 1 106A may measure ambient temperature, remote sensor 2 106B may measure relative humidity, remote sensor 3 106C may be a biohazard detector, and remote sensor 4 106D may be a motion detector for sensing combatant movements. All sensor data is processed by the monitor station 102 and assessed to determine whether a dangerous condition is indicated. If a dangerous condition is indicated, the monitor station 102 may signal a remote alert device 108 carried by the soldier 1104.

c. Soldier in Extreme Operational Environment

In another example, the monitor system 100 may be used to assess the condition of a soldier 1104 moving through an extreme operational environment. In this example, the soldier may carry an affixed sensor device 104 that may further receive additional sensor signals from an array of additional remote sensors 106A-106D. In this example, as in the previous example discussed herein above, remote sensor 1 106A may measure ambient temperature, remote sensor 2 106B may measure relative humidity, remote sensor 3 106C may be a biohazard detector, and remote sensor 4 106D may be a motion detector for sensing combatant movements. The affixed sensor device 104 may continuously receive and process sensor data from internal and remote sensors, and assess whether the sensor data indicate a dangerous condition.

If a dangerous condition is indicated, the affixed sensor device 104 may produce an alert signal to inform the soldier of the dangerous condition. In addition, the affixed sensor device may communicate the alert signal to the monitor station 102, which may be located back at the soldier's base of operations, to communicate the soldier's situation to the soldier's commanders.

EXAMPLES

The following examples illustrate various embodiments of the invention.

Example 1

Wireless Communications Testing

To demonstrate the feasibility of wireless communication between remote environmental sensors and a monitor station, the following experiments were conducted.

Two breadboard circuits were developed that included identical circuit schematics: PIC18F4550 microcontroller (Microchip Technology Inc., Chandler, Ariz., USA), a TI CC1101 wireless module (Texas Instruments Inc., Dallas, Tex., USA), and a set of eight red LEDs. The LEDs served as a visual display of the register values being transmitted and received by both circuits, and to facilitate troubleshooting of the circuits. The microcontroller and wireless module were similar to the microcontrollers and wireless modules selected for inclusion in the components of a prototype monitor system.

The microcontroller of the first breadboard circuit was loaded with a program that would configure that circuit's wireless module in transmitter mode. The microcontroller of the second breadboard circuit was loaded with a program that configured the second circuit's wireless module in receive mode. The first and second breadboard circuits served as the transmitter and receiver, respectively, of a prototype wireless network.

The prototype wireless network successfully transmitted data over a distance of roughly 600 meters across a university campus. Further, the prototype wireless network successfully transmitted data though several concrete walls and floors within a university research building and in the presence of electrical interference.

The results of these experiments demonstrated the feasibility of wireless communication between remote environmental sensors and a monitor station, and further provided an initial evaluation of the potential range of movement for a variety of different sensor and monitor station designs.

Example 2

Skin Surface Temperature Testing

To assess the feasibility of measuring the skin temperature of a canine, the following experiment was conducted.

A prototype circuit that included a thermistor (HSTH-44304, Omega, Inc.) in an unbalanced Wheatstone bridge circuit and a PIC18F4550 microcontroller Microchip Technology Inc., Chandler, Ariz., USA) was used to test the skin temperature of three canine subjects at several locations: the ventral neck, the dorsal neck, and axillary. For comparison, a core temperature was obtained by measuring the rectal temperature of all canine subjects. In addition, similar temperature measurements were made from one of the canine subjects while exercising.

The temperature measurements obtained for the canine subjects are summarized in Table 1 below. For all dogs at rest, the skin temperate varied depending on the location at which the temperature measurement was obtained. Typically, the ventral neck skin temperature was lowest, the axillary skin temperature was highest, and the dorsal neck skin temperature fell between the ventral neck and axillary skin temperatures. The skin temperature of the dogs was consistently about 3° F. lower than the corresponding core temperature, as estimated from the measured rectal temperatures.

TABLE 1

Skin and Core Temperature Measurements for Three Canines

| Subject | Skin Temperature (° F.) | | | Rectal Temp. (° F.) |
|---|---|---|---|---|
| | Ventral Neck | Dorsal Neck | Axillary | |
| Dog 1 | 97.7 | 98.3 | 99.4 | 101.5 |
| | 97.7 | 98.8 | 99.4 | |
| | 98.3 | 99.1 | 99.4 | |
| Average | 97.9 | 98.73333 | 99.4 | |
| Dog 1 (during exercise) | 97.3 | 97.3 | 99.4 | 101.5 |

TABLE 1-continued

Skin and Core Temperature Measurements for Three Canines

| Subject | Skin Temperature (° F.) | | | Rectal Temp. (° F.) |
| --- | --- | --- | --- | --- |
| | Ventral Neck | Dorsal Neck | Axillary | |
| Dog 2 | 96 | 97.2 | 98 | 100.8 |
| | 96.3 | 97.7 | 99.2 | |
| | 96.7 | 97.4 | 99.1 | |
| Average | 96.3 | 97.4 | 98.8 | |
| Dog 3 | 89.5 | 97.1 | 99.5 | 100.3 |
| | 95.8 | 97.9 | 98 | |
| | 97.1 | 97.4 | 98.3 | |
| Average | 94.1 | 97.5 | 98.6 | |

During exercise, the ventral neck and dorsal neck temperatures decreased 0.6° F. and about 1.4° F., respectively, relative to the resting temperature, and core temperature and axillary skin temperature remained the same. This result was unexpected, because physiological theory predicts that activity would induce a rise in core temperature and a subsequent rise in skin temperature.

The results of this experiment demonstrated that the skin temperature of canines could be consistently measured using a prototype thermocouple temperature sensor. However, the relationship between canine skin temperature and core temperature may be a complex relationship influenced by the location of the skin on the dog's body as well as the dog's activity level.

It should be understood from the foregoing that, while particular embodiments have been illustrated and described, various modifications can be made thereto without departing from the spirit and scope of the invention as will be apparent to those skilled in the art. Such changes and modifications are within the scope and teachings of this invention as defined in the claims appended hereto.

What is claimed is:

1. A monitor system for monitoring at least one condition of an animal in an extreme environment, comprising:
    at least one physiological sensor to measure at least one physiological measurement from the animal;
    at least one environmental sensor to measure at least one environmental measurement from a region near the animal;
    at least one processor;
    a database comprising:
        at least one threshold value, wherein the at least one threshold value comprises a maximum safe value of the at least one condition of the animal, and wherein the at least one threshold value is a function of at least one condition of the animal; and
        at least one data quality criterion; and
    an application executed by the processor to:
        select a subset of the at least one physiological measurement and the at least one environmental measurement based on the at least one data quality criterion;
        calculate the at least one condition of the animal using the subset of the at least one physiological measurement and the at least one environmental measurement;
        retrieve the at least one threshold value;
        compare the at least one condition of the animal to the at least one threshold value, wherein each threshold value comprises the maximum safe value of each of the at least one conditions of the animal; and
        produce an alarm signal if the at least one condition of the animal exceeds the at least one threshold value.

2. The system of claim 1, wherein the at least one condition of the animal comprises any one or more of: core temperature, heat index, perceived temperature, wind chill, physiological stress, or activity level.

3. The system of claim 1, wherein the at least one threshold value comprises a maximum safe core temperature, wherein the maximum safe core temperature varies depending on the activity level of the animal.

4. The system of claim 1, wherein:
    the at least one environmental measurement comprises any one or more of: ambient temperature, relative humidity, or wind speed; and
    the at least one physiological measurement comprises any one or more of: skin temperature, respiration rate, heart rate, or accelerometer readings.

5. The system of claim 1, wherein at least one data quality criterion comprises any one or more of: a range of valid data values, a maximum variance of the data, or a minimum data measurement rate.

6. The system of claim 1, wherein selection of the subset of the at least one physiological measurement and the at least one environmental measurement comprises any one or more of: eliminating redundant measurements; selecting a highest quality measurement for each of the at least one physiological measurements and each of the at least one environmental measurements; or eliminating a measurement determined to be an invalid measurement.

7. The system of claim 6, wherein eliminating redundant measurements comprises any one or more of: selecting a highest or lowest measurement; selecting a measurement with a lowest variability; calculating an average of the redundant measurements; or calculating a weighted average of the redundant measurements.

8. A method for monitoring at least one condition of an animal in an extreme environment, comprising:
    receiving at least one physiological measurement from the animal;
    receiving at least one environmental measurement from a region near the animal;
    selecting a subset of the at least one physiological measurement and the at least one environmental measurement based on at least one data quality criterion;
    retrieving at least one threshold value from a memory of at least one processor, wherein the at least one threshold value comprises the maximum safe value of the at least one condition of the animal, and wherein the at least one threshold value is a function of at least one condition of the animal;
    calculating at least one condition of the animal using the subset of the at least one physiological measurement and the at least one environmental measurement;
    comparing the at least one condition of the animal to the at least one threshold value, wherein each threshold value comprises the maximum safe value of each of the at least one conditions of the animal; and
    producing an alarm signal if the at least one condition of the animal exceeds the at least one threshold value.

9. The method of claim 8, wherein the at least one condition of the animal comprises any one or more of: heat index, perceived temperature, wind chill, core temperature, physiological stress, or activity level.

10. The method of claim 8, wherein the at least one threshold value comprises a maximum safe core temperature, wherein the maximum safe core temperature varies depending on the activity level of the animal.

11. The method of claim 8, wherein:
the at least one environmental measurement comprises any one or more of: ambient temperature, relative humidity, or wind speed; and
the at least one physiological measurement comprises any one or more of: skin temperature, respiration rate, heart rate, or accelerometer readings.

12. The system of claim 8, wherein at least one data quality criterion comprises any one or more of: a range of valid data values, a maximum variance of the data, or a minimum data measurement rate.

13. The system of claim 8, wherein selection of the subset of the at least one physiological measurement and the at least one environmental measurement comprises any one or more of: eliminating redundant measurements; selecting a highest quality measurement for each of the at least one physiological measurements and each of the at least one environmental measurements; or eliminating a measurement determined to be an invalid measurement.

14. The method of claim 13, wherein eliminating redundant measurements comprises any one or more of: selecting a highest or lowest measurement; selecting a measurement with a lowest variability; calculating an average of the redundant measurements; or calculating a weighted average of the redundant measurements.

15. A method for monitoring at least one condition of an animal in an extreme environment, comprising:
receiving a skin temperature and an accelerometer reading from the animal;
receiving an ambient temperature and a relative humidity from a region near the animal;
calculating an activity level of the animal by comparing the accelerometer reading to an animal activity rule;
retrieving a maximum core temperature, wherein the maximum core temperature is a function of the animal activity level;
calculating a core temperature by substituting the skin temperature into a core temperature rule;
calculating a heat index by substituting the ambient temperature and relative humidity into a heat index rule;
retrieving a maximum heat index; and
producing an alarm signal if the core temperature is greater than or equal to the maximum core temperature and/or the heat index is greater than or equal to the maximum heat index.

16. The method of claim 15, wherein the maximum core temperature comprises a maximum core temperature for an active animal and a maximum core temperature for a non-active animal.

17. The method of claim 16, wherein maximum core temperature is a function of the animal activity level and the heat index.

18. The method of claim 15, wherein the animal activity rule comprises defining the animal activity level as active when an accelerometer reading is greater than a maximum non-active accelerometer reading, and defining animal activity level as non-active when an accelerometer reading is less than or equal to a maximum non-active accelerometer reading.

* * * * *